(12) United States Patent
Yu et al.

(10) Patent No.: US 9,091,637 B2
(45) Date of Patent: Jul. 28, 2015

(54) SMART FIBER OPTIC SENSORS SYSTEMS AND METHODS FOR QUANTITATIVE OPTICAL SPECTROSCOPY

(75) Inventors: Bing Yu, Cary, NC (US); Nirmala Ramanujam, Chapel Hill, NC (US)

(73) Assignee: DUKE UNIVERSITY, Durham, NC (US)

( * ) Notice: Subject to any disclaimer, the term of this patent is extended or adjusted under 35 U.S.C. 154(b) by 342 days.

(21) Appl. No.: 13/513,458

(22) PCT Filed: Dec. 6, 2010

(86) PCT No.: PCT/US2010/059140
§ 371 (c)(1),
(2), (4) Date: Sep. 18, 2012

(65) Prior Publication Data
US 2013/0100439 A1      Apr. 25, 2013

Related U.S. Application Data

(60) Provisional application No. 61/266,843, filed on Dec. 4, 2009.

(51) Int. Cl.
*G01N 21/00*      (2006.01)
*G01N 21/25*      (2006.01)
(Continued)

(52) U.S. Cl.
CPC .......... *G01N 21/255* (2013.01); *A61B 5/0075* (2013.01); *A61B 5/0084* (2013.01); *A61B 5/6885* (2013.01); *G01J 3/0218* (2013.01); *G01J 3/28* (2013.01); *G01J 3/42* (2013.01); *G01L 9/0079* (2013.01); *G01N 21/274* (2013.01);
(Continued)

(58) Field of Classification Search
USPC ...................................... 356/72–73
See application file for complete search history.

(56) References Cited

U.S. PATENT DOCUMENTS

| 4,580,895 A | 4/1986 | Patel |
|---|---|---|
| 5,125,747 A | 6/1992 | Sayegh et al. |

(Continued)

FOREIGN PATENT DOCUMENTS

| WO | WO 02/26152 A1 | 4/2002 |
|---|---|---|
| WO | WO 02/40971 A1 | 5/2002 |

(Continued)

OTHER PUBLICATIONS

Restriction Requirement for U.S. Appl. No. 12/680,302 (Mar. 28, 2013).

(Continued)

*Primary Examiner* — Abdullahi Nur
(74) *Attorney, Agent, or Firm* — Jenkins, Wilson, Taylor & Hunt, P.A.

(57) ABSTRACT

Smart fiber optic sensors, systems, and methods for performing quantitative optical spectroscopy are disclosed. In one embodiment, smart fiber optic sensor can include a sensing channel, a calibration channel, and a pressure sensing channel. External force or pressure can be calculated at pressure sensing channel for monitoring and controlling pressure at a sensor-specimen interface thereby ensuring more accurate specimen spectral data is collected. Contact pressure can be adjusted to remain within a specified range. A calibration light of the calibration channel and an illumination light of the sensing channel can be generated simultaneously from a shared light source. Pressure sensing channel can transmit light from a second light source and collect pressure spectral data.

25 Claims, 7 Drawing Sheets

(51) Int. Cl.
*G01N 21/27* (2006.01)
*G01J 3/28* (2006.01)
*G01J 3/42* (2006.01)
*G01J 3/02* (2006.01)
*A61B 5/00* (2006.01)
*G01L 9/00* (2006.01)
*G01N 21/64* (2006.01)

(52) U.S. Cl.
CPC .............. *A61B 5/4331* (2013.01); *A61B 5/4552* (2013.01); *A61B 2560/0228* (2013.01); *G01N 21/645* (2013.01); *G01N 2201/0627* (2013.01); *G01N 2201/08* (2013.01)

(56) References Cited

U.S. PATENT DOCUMENTS

| | | | |
|---|---|---|---|
| 5,186,714 | A | 2/1993 | Boudreault et al. |
| 5,439,578 | A | 8/1995 | Dovichi et al. |
| 5,452,723 | A | 9/1995 | Wu et al. |
| 5,582,168 | A | 12/1996 | Samuels et al. |
| 5,792,049 | A | 8/1998 | Eppstein et al. |
| 5,813,403 | A | 9/1998 | Soller et al. |
| 5,924,981 | A | 7/1999 | Rothfritz et al. |
| 5,953,477 | A | 9/1999 | Wach et al. |
| 5,983,125 | A | 11/1999 | Alfano et al. |
| 6,052,177 | A | 4/2000 | Millar et al. |
| 6,055,451 | A | 4/2000 | Bambot et al. |
| 6,219,566 | B1 | 4/2001 | Weersink et al. |
| 6,351,306 | B1 | 2/2002 | Tedesco et al. |
| 6,377,840 | B1 | 4/2002 | Gritsenko et al. |
| 6,411,373 | B1 | 6/2002 | Garside et al. |
| 6,549,284 | B1 | 4/2003 | Boas et al. |
| 6,564,088 | B1 | 5/2003 | Soller et al. |
| 6,571,118 | B1 | 5/2003 | Utzinger et al. |
| 6,577,391 | B1 | 6/2003 | Faupel et al. |
| 6,590,651 | B1 | 7/2003 | Bambot et al. |
| 6,662,030 | B2 | 12/2003 | Khalil et al. |
| 6,678,541 | B1 | 1/2004 | Durkin et al. |
| 6,813,515 | B2 | 11/2004 | Hashimshony |
| 6,825,928 | B2 | 11/2004 | Liu et al. |
| 6,850,656 | B1 | 2/2005 | Bevilacqua et al. |
| 6,870,620 | B2 | 3/2005 | Faupel et al. |
| 6,912,412 | B2 | 6/2005 | Georgakoudi et al. |
| 6,975,899 | B2 | 12/2005 | Faupel et al. |
| 7,006,220 | B2 | 2/2006 | Bambot et al. |
| 7,030,988 | B2 | 4/2006 | Kubo et al. |
| 7,064,837 | B2 | 6/2006 | Mori et al. |
| 7,082,325 | B2 | 7/2006 | Hashimshony et al. |
| 7,113,624 | B2 | 9/2006 | Curry |
| 7,129,454 | B2 | 10/2006 | O'Connell et al. |
| 7,145,645 | B2 | 12/2006 | Blumenfeld et al. |
| 7,184,824 | B2 | 2/2007 | Hashimshony |
| 7,202,947 | B2 | 4/2007 | Liu et al. |
| 7,236,815 | B2 | 6/2007 | Richards-Kortum et al. |
| 7,333,189 | B2 | 2/2008 | Fulghum et al. |
| 7,403,812 | B2 | 7/2008 | Rice et al. |
| 7,411,680 | B2 | 8/2008 | Chang et al. |
| 7,570,988 | B2 | 8/2009 | Ramanujam et al. |
| 7,751,039 | B2 | 7/2010 | Ramanujam et al. |
| 7,818,154 | B2 | 10/2010 | Palmer et al. |
| 7,835,786 | B2 | 11/2010 | Palmer et al. |
| 7,952,704 | B2 | 5/2011 | Ramanujam et al. |
| 8,804,115 | B2 | 8/2014 | Yu et al. |
| 2002/0055671 | A1 | 5/2002 | Wu et al. |
| 2002/0114734 | A1 | 8/2002 | Pantoliano et al. |
| 2003/0220549 | A1 | 11/2003 | Liu et al. |
| 2004/0010192 | A1 | 1/2004 | Benaron et al. |
| 2004/0015375 | A1 | 1/2004 | Schomacker et al. |
| 2004/0015062 | A1 | 1/2004 | Ntziachristos et al. |
| 2004/0064053 | A1 | 4/2004 | Chang et al. |
| 2004/0162489 | A1 | 8/2004 | Richards-Kortum et al. |
| 2004/0168692 | A1 | 9/2004 | Fogarty et al. |
| 2004/0218172 | A1 | 11/2004 | DeVerse et al. |
| 2005/0030372 | A1 | 2/2005 | Jung et al. |
| 2005/0143663 | A1 | 6/2005 | Liu et al. |
| 2005/0162646 | A1 | 7/2005 | Tedesco et al. |
| 2005/0203419 | A1 | 9/2005 | Ramanujam et al. |
| 2006/0114457 | A1 | 6/2006 | Schmitz et al. |
| 2007/0019199 | A1 | 1/2007 | Palmer et al. |
| 2007/0201788 | A1 | 8/2007 | Liu et al. |
| 2007/0282575 | A1 | 12/2007 | Gossage |
| 2008/0270091 | A1 | 10/2008 | Ramanujam et al. |
| 2009/0015826 | A1 | 1/2009 | Ramanujam et al. |
| 2009/0204009 | A1* | 8/2009 | Powers et al. .................. 600/476 |
| 2011/0059016 | A1 | 3/2011 | Ramanujam et al. |
| 2011/0105865 | A1 | 5/2011 | Yu et al. |
| 2011/0112435 | A1 | 5/2011 | Ramanujam et al. |
| 2011/0295541 | A1 | 12/2011 | Yu et al. |

FOREIGN PATENT DOCUMENTS

| | | |
|---|---|---|
| WO | WO 2006/059226 A1 | 6/2006 |
| WO | WO 2006/076810 A1 | 7/2006 |
| WO | WO 2007/109126 A2 | 9/2007 |
| WO | WO 2007/126827 A2 | 11/2007 |
| WO | WO 2008/103486 A1 | 8/2008 |
| WO | WO 2009/043045 A1 | 4/2009 |
| WO | WO 2009/043050 A2 | 4/2009 |
| WO | WO 2009/132360 A2 | 10/2009 |
| WO | WO 2010/042249 A2 | 4/2010 |

OTHER PUBLICATIONS

Non-Final Office Action for U.S. Appl. No. 12/989,595 (Mar. 20, 2013).
Communication Pursuant to Article 94(3) EPC for European Patent Application No. 07753265.3 (Feb. 27, 2013).
Communication Pursuant to Article 94(3) EPC for European Patent Application No. 07753265.3 (Apr. 12, 2012).
Communication pursuant to Article 94(3) EPC for European Applciation No. 07 753 265.3 (Mar. 18, 2011).
Extended European Search Report for European Application No. 07754152.2 (Feb. 15, 2011).
Notice of Allowance and Fee(s) Due for U.S. Appl. No. 12/830,078 (Jan. 26, 2011).
Non-Final Official Action for U.S. Appl. No. 12/830,078 (Oct. 4, 2010).
Non-Final Official Action for U.S. Appl. No. 12/036,717 (Aug. 17, 2010).
Communication pursuant to Article 94(3) for European Patent No. 2001352 (Jul. 13, 2010).
Notice of Allowance and Fee(s) Due for U.S. Appl. No. 11/493,020 (Jul. 6, 2010).
Notice of Allowance and Fee(s) Due for U.S. Appl. No. 11/725,141 (Jun. 11, 2010).
Notification of Transmittal of the International Search Report and the Written Opinion of the International Searching Authority, or the Declaration for International Application No. PCT/US2009/041732 (Apr. 15, 2010).
Notice of Allowance and Fee(s) Due for U.S. Appl. No. 11/493,020 (Mar. 19, 2010).
Extended European Search Report for European Patent No. 2001352 (Mar. 5, 2010).
Notice of Allowance and Fee(s) Due for U.S. Appl. No. 11/725,141 (Feb. 22, 2010).
Notice of Allowance and Fee(s) Due for U.S. Appl. No. 11/729,967 (Feb. 19, 2010).
Interview Summary for U.S. Appl. No. 11/493,020 (Nov. 17, 2009).
Interview Summary for U.S. Appl. No. 11/725,141 (Nov. 17, 2009).
Notice of Allowance and Fee(s) Due for U.S. Appl. No. 11/729,967 (Oct. 22, 2009).
Interview Summary for U.S. Appl. No. 11/729,967 (Sep. 24, 2009).
Official Action for U.S. Appl. No. 11/725,141 (Jun. 12, 2002).
Official Action for U.S. Appl. No. 11/729,967 (May 28, 2009).
Notice of Allowance and Fee(s) Due for U.S. Appl. No. 11/119,865 (May 1, 2009).
Office Action for U.S. Appl. No. 11/493,020 (Apr. 24, 2009).
Restriction and/or Election Requirement for U.S. Appl. No. 11/729,967 (Apr. 17, 2009).

(56) References Cited

OTHER PUBLICATIONS

Notification of Transmittal of the International Search Report and the Written Opinion of the International Searching Authority, or the Declaration for International Application No. PCT/US2008/078194 (Apr. 17, 2009).
Final Official Action for U.S. Appl. No. 11/119,865 (Mar. 18, 2009).
Notification of Transmittal of the International Search Report and the Written Opinion of the International Searching Authority, or the Declaration for International Application No. PCT/US2008/078186 (Feb. 17, 2009).
Restriction and/or Election Requirement for U.S. Appl. No. 11/493,020 (Feb. 10, 2009).
Communication of European Publication Number and Information on the Application of Article 67(3) EPC for European Patent No. 2005173 (Nov. 26, 2008).
Communication of European Publication Number and Information on the Application of Article 67(3) EPC for European Patent No. 2001352 (Nov. 19, 2008).
Notification of Transmittal of the International Search Report and the Written Opinion of the International Searching Authority, or the Declaration for International Application No. PCT/US07/07586 (Oct. 7, 2008).
Non-Final Official Action for U.S. Appl. No. 11/119,865 (Jul. 11, 2008).
Notification of Transmittal of the International Search Report and the Written Opinion of the International Searching Authority, or the Declaration for International Application No. PCT/US08/02431 (Jun. 19, 2008).
Notification of Transmittal of the International Search Report and the Written Opinion of the International Searching Authority, or the Declaration for International Application No. PCT/US06/28770 (Mar. 12, 2008).
Communication of European Publication Number and Information on the Application of Article 67(3) EPC for European Application No. 06800300.3 (Mar. 12, 2008).
Notification of Transmittal of the International Search Report and Written Opinion of the International Searching Authority, or the Declaration corresponding to PCT application No. PCT/US07/06624 (Feb. 7, 2008).
(Quan) Liu et al., "Experimental Proof of the Feasibility of Using an Angled Fiber-optic Probe for Depth-sensitive Flurorescence Spectroscopy of Turbid Media," Optics Letters, vol. 29, No. 17, pp. 2034-2036 (Sep. 1, 2004).
Amelink et al., "Noninvasive measurement of the morphology and physiology of oral mucosa by use of optical spectroscopy," Oral Oncol, 44(1): p. 65-71 (2008).
Amelink et al., "In vivo Measurement of the Local Optical Properties of Tissue by use of Differential Path-Length Spectroscopy," Optics Letters, vol. 29, No. 10, pp. 1087-1089 (May 15, 2004).
Amelink et al., "Measurement of the Local Optical Properties of Turbid Media by Differential Path-Length Spectroscopy," Applied Optics, vol. 34, No. 15, pp. 3048-3054 (May 20, 2004).
Arifler et al., "Spatially resolved reflectance spectroscopy for diagnosis of cervical precancer: Monte Carlo modeling and comparison to clinical measurements," J Biomed Opt, 11(6): p. 064027 (Nov./Dec. 2006).
Arifler et al., "Reflectance spectroscopy for diagnosis of epithelial precancer: model-based analysis of fiber-optic probe designs to resolve spectral information from epithelium and stroma," Appl Opt, 44(20): p. 4291-305 (Jul. 2005).
Bender et al., "A robust Monte Carlo model for the extraction of biological absorption and scattering in vivo," IEEE Trans Biomed Eng, 56(4): p. 960-8 (Apr. 2009).
Bevilacqua et al., "Monte Carlo study of diffuse reflectance at source-detector separations close to one transport mean free path," J. Opt. Soc. Am. A., vol. 16, No. 12, pp. 2935-2945 (Dec. 1999).
Bigio et al., "Spectroscopic sensing of cancer and cancer therapy: current status of translational research," Cancer Biol Ther 3(3): 259-67, (2004).
Bigio et al., "Diagnosis of breast cancer using elastic-scattering spectroscopy: preliminary clinical results," Journal of Biomedical Optics, 5(2): pp. 221-228 (2000).
Biswal et al., "Recovery of Turbidity Free Fluorescence from Measured Fluorescence: An Experimental Approach," Optics Express, vol. 11, No. 24, pp. 3320-3331 (Dec. 1, 2003).
Bohnert et al., "A Monte Carol-based Model for Steady-state Diffuse Reflectance Spectrometry in Huamn Skin: Estimation of Carbon Monoxide Concentration in Livor Morits," International Journal of Legal and Medicine vol. 119, pp. 355-362 (2005).
Bolin et al., "Refractive Index of Some Mammalian Tissues Using a Fiber Optic Cladding Method," Applied Optics, vol. 28, No. 12, pp. 2297-2303 (Jun. 15, 1989).
Breslin et al., "Autofluorescence and Diffuse Reflectance Properties of Malignant and Benign Breast Tissues," Annals of Surgical Oncology, vol. 11, No. 1, pp. 65-70 (2003).
Cardenas-Turanzas et al., "The clinical effectiveness of optical spectroscopy for the in vivo diagnosis of cervical intraepithelial neoplasia: where are we ?" Gynecol Oncol, 107(1 Suppl 1): p. S138-46 (2007).
CDC Oral Cancer Background Papers, http://www.oralcancerfoundation.org/cdc/index.htm, (retrieved on Feb. 27, 2013).
Cerussi et al., "In vivo absorption, scattering, and physiologic properties of 58 malignant breast tumors determined by broadband diffuse optical spectroscopy," J Biomed Opt 11 :044005 (2006).
Chan et al., "Effects of compression on soft tissue optical properties," Selected Topics in Quantum Electronics, IEEE Journal of, 2(4): p. 943-950 (Dec. 1996).
Chance et al., "Biochemical Distinctions Between Normal and Cancerous Human Breast Tissues Obtained from Fluorescence Spectroscopy," Proceedings of Optical Tomography and Spectroscopy of Tissue: Theory, Instrumentation, Model and Human Studies II. Biomedical Optics, vol. 2979, pp. 585-588 (Feb. 9-12, 1997).
Chang et al., "Quantitative physiology of the precancerous cervix in vivo through optical spectroscopy," Neoplasia, 11(4): p. 325-32 (Apr. 2009).
Chang et al., "Combined reflectance and fluorescence spectroscopy for in vivo detection of cervical pre-cancer," J Biomed Opt, 10(2): p. 024031 (Mar./Apr. 2005).
Chang et al., "Analytical Model to Describe Fluorescence Spectra of Normal and Preneoplastic Epithelial Tissue: Comparison with Monte Carlo Simulations and Clinical Measurements," Journal of Biomedical Optics, vol. 9, No. 3, pp. 511-522 (May/Jun. 2004).
Collier et al., "Determination of epithelial tissue scattering coefficient using confocal microscopy," IEEE J. Sel. Topics Quantum Electron. 9, 307-313 (2003).
Diamond et al., "Measurement of Fluorophore Concentrations and Fluorescence Quantum Yield in Tissue-Simulating Phantoms Using Three Diffusion Models of Steady-State Spatially Resolved Fluorescence," Physics in Medicine and Biology, vol. 48, pp. 4135-4149 (2003).
Diamond et al., "Quantification of Fluorophore Concentration in Tissue-Simulating Media by Fluorescence Measurements with a Single Optical Fiber," Applied Optics, vol. 42, No. 13, pp. 2436-2444 (May 1, 2003).
Farkas et al., "Applications of spectral imaging: detection and analysis of human melanoma and its precursors," Pigment Cell Res 14(1): 2-8. (2001).
Finlay et al., "Hemoglobin Oxygen Saturations in Phantoms and In Vivo from Measurements of Steady State Diffuse Reflectance at a Single, Short Source-detector Separation," Med Phys. vol. 31, No. 7, pp. 1949-1959 (Jul. 2004).
Follen et al., "Optical technologies for cervical neoplasia: update of an NCI program project grant," Clin Adv Hematol Oncol, 3(1): p. 41-53 (2005).
Freeberg et al., "The performance of fluorescence and reflectance spectroscopy for the in vivo diagnosis of cervical neoplasia; point probe versus multispectral approaches," Gynecol Oncol, 107(1 Suppl 1): p. S248-55 (2007).
Gardner et al., "Fluorescence Spectroscopy of Tissue: Recovery of Intrinsic Fluorescence from Measured Fluorescence," Applied Optics, vol. 35, No. 10, pp. 1780-1792 (Apr. 1, 1996).

(56) References Cited

OTHER PUBLICATIONS

Georgakoudi et al., "Trimodal spectroscopy for the detection and characterization of cervical precancers in vivo," Am J Obstet Gynecol, 186(3): p. 374-82 (2002).
Graaff et al., "Condensed Monte Carlo Simulations for the Descriptions of Light Transport," Applied Optics, vol. 32, No. 4, pp. 426-434 (Feb. 1, 1993).
Gunn, "Support Vector Machines for Classificiation and Regression," University of Southampton, Department of Electronics and Computer Science, http://homepages.cae.wisc.edu/~ece539/software/svmtoolbox/svm.pdf (May 14, 1998).
Hasina et al., "Angiogenesis in oral cancer," J Dent Educ, 65(11): p. 1282-90 (2001).
Kienle et al., "Spatially resolved absolute diffuse reflectance measurements for noninvasive determination of the optical scattering and absorption coefficients of biological tissue," Applied Optics, vol. 35, No. 13, pp. 2304-2314 (May 1, 1996).
Kienle et al., "Determination of the Optical Properties of Turbid Media From a Single Monte Carlo Simulation," Physics in Medicine and Biology, vol. 41, Issue 10, p. 2221-2227 (Oct. 1996).
Lane et al., "Simple device for the direct visualization of oral-cavity tissue fluorescence," J Biomed Opt, 11(2): p. 024006 (Mar./Apr. 2006).
Liu et al., "Experimental proof of the feasibility of using an angled fiber-optic probe for the depth-sensitive fluorscence spectroscopy of turbid media," Opt Lett, 29(17): p. 2034-6 (Sep. 2004).
Liu et al., "Experimental Validation of Monte Carlo Modeling of Fluorescence in Tissues in the UV-Visible Spectrum," Journal of Biomedical Optics, vol. 8, No. 2, pp. 223-236 (Apr. 2003).
Liu et al., "Relationship Between Depth of a Target in a Turbid Medium and Fluorescence Measured by a Variable-Aperture Method," Optics Letters, vol. 27, Issue 2, pp. 104-106 (Jan. 15, 2002).
Liu et al., "Scaling Method for Fast Monte Carlo Simulation of Diffuse Reflectance Spectra from Multilayered Turbid Media," J. Opt. Soc. Am. A, vol. 24, No. 4, pp. 1011-1025 (Apr. 2007).
Liu et al., "Sequential Estimation of Optical Properties of a Two-layered Epithelial Tissue Model from Depth-Resolved Ultraviolet-visible Diffuse Relectance Spectra," Applied Optics, vol. 45, No. 19, pp. 4776-4790 (Jul. 1, 2006).
Manos et al., "Optical Fiber Design Using Evolutionary Strategies," Engineering Computations, vol. 21, No. 6, pp. 564-576 (2004).
Marin et al., "Calibration standards for multicenter clinical trials of fluorescence spectroscopy for in vivo diagnosis," J Biomed Opt, 11(1): p. 014010 (2006).
Marin et al., "Diffuse reflectance patterns in cervical spectroscopy," Gynecol Oncol, 99(3 Suppl 1): p. S116-20 (2005).
McClain et al., "Optical Absorption and Fluorescence Spectral Imaging Using Fiber Bundle Image Compression," Applied Spectroscopy, 53(9):1118-1122 (1999).
Mirabal et al., "Reflectance spectroscopy for in vivo detection of cervical precancer," J Biomed Opt 7(4): 587-94, (2002).
Mourant et al., "Measuring Absorption Coeffcients in Small Volumes of Highly Scattering Media: Source-Detector Separations for Which Path Lengths do not Depend on Scattering Properties," Applied Optics, vol. 36, No. 22, pp. 5655-5661 (Aug. 1, 1997).
Muller et al., "Spectroscopic detection and evaluation of morphologic and biochemical changes in early human oral carcinoma," Cancer, 97(7): p. 1681-92 (2003).
Müller et al., "Intrinsic Fluorescence Spectroscopy in Turbid Media: Disentangling Effects of Scattering and Adsorption," Applied Optics, vol. 40, No. 25, pp. 4633-4646 (Sep. 1, 2001).
Nichols et al., "Design and testing of a white-light steady-state diffuse reflectance spectrometer for determination of optical properties of highly scattering systems," Appl. Opt. 36(1), pp. 93-104 (1997).
Palmer et al., "Comparison of Multiexcitation Fluorescence and Diffuse Reflectance Spectroscopy for the Diagnosis of Breast Cancer," Biomedical Engineering, vol. 50, Issue 11, pp. 1233-1242 (Nov. 2003).
Palmer et al., "Diagnosis of Breast Cancer Using Optical Spectroscopy," Medical Laser Appl. 18: 233-248 (2003).
Palmer et al., "Monte Carlo-Based Inverse Model for Calculating Tissue Optical Properties. Part I: Theory and Validation on Synthetic Phantoms," Applied Optics, vol. 45, No. 5, pp. 1062-1071 (Feb. 10, 2006).
Palmer et al., "Monte Carlo-Based Inverse Model for Calculating Tissue Optical Properties. Part II: Application to Breast Cancer Diagnosis," Applied Optics, vol. 45, No. 5, pp. 1072-1078 (Feb. 10, 2006).
Palmer et al., "Optimal Methods for Fluorescence and Diffuse Reflectance Measurements of Tissue Biopsy Samples," Lasers in Surgery and Medicine, vol. 30, pp. 191-200 (2002).
Palmer, "Experimental, Computational, and Analytical Techniques for Diagnosing Breast Cancer Using Optical Spectroscopy," Dissertation, University of Wisconsin-Madison, pp. 1-188 (2005).
Pavlova et al., "Fluorescence spectroscopy of oral tissue: Monte Carlo modeling with site-specific tissue properties," J Biomed Opt, 14(1): p. 014009 (Jan./Feb. 2009).
Pfefer et al., "Influence of Illumination-Collection Geometry on Fluorescence Spectroscopy in Multilayer Tissue," Medical and Biological Engineering and Computing, vol. 42, No. 5, pp. 669-673 (Sep. 2004).
Pfefer et al., "Oblique-Incidence Illumination and Collection of Depth-Selective Fluorescence Spectroscopy," Journal of Biomedical Optics, vol. 10, No. 4, (Jul./Aug. 2005).
Pfefer et al., "Reflectance-based Determination of Optical Properties in Highly Attenuating Tissue," Journal of Biomedical Optics, vol. 8, Issue 2 (Apr. 2003).
Pfefer, et al., "Selective Detection of Fluorophore Layers in Turbid Media: The Role of Fiber-Optic Probe Design," Optics Letters, vol. 28, Issue 2, pp. 12-122 (Jan. 15, 2003).
Pogue et al., "Fiber-Optic Bundle Design for Quantitative Fluorescence Measurement from Tissue," Applied Optics, vol. 37, Issue 31, pp. 7429-7436 (Nov. 1, 1998).
Prahl, "Mie scattering program," Oregon Medical Laser Center, available at http://omlc.ogi.edu/software/mie/index.html (2005) (Printed from the Internet Feb. 26, 2013).
Prahl, "Mie Scattering Program," vol. 2003 (Copright 2007) (Downloaded from the Internet on Jan. 19, 2010).
Qi et al., "Novel data processing techniques for dispersive white light interferometer," Opt Eng. 42: p. 3165-3171 (Nov. 2003).
Rahman et al., "Low-cost, multimodal, portable screening system for early detection of oral cancer," J Biomed Opt, 13(3): p. 030502 (May/Jun. 2008).
Ramanujam, "Fluorescence Spectroscopy in Vivo," Encyclopedia of Analytical Chemistry, pp. 20-56 (2000).
Ramanujam, "Fluorescence Spectroscopy of Neoplastic and Non-Neoplastic Tissues," Neoplasia, vol. 2, Nos. 1-2, pp. 89-117 (Jan.-Apr. 2000).
Reif et al., "Analysis of changes in reflectance measurements on biological tissues subjected to different probe pressures," J Biomed Opt, 13(1): p. 010502 (Jan./Feb. 2008).
Saslow et al., "American Cancer Society Guideline for the Early Detection of Cervical Neoplasia and Cancer," CA Cancer J Clin, 52, pp. 342-362 (2002).
Schwarz et al., "Autofluorescence and diffuse reflectance spectroscopy of oral epithelial tissue using a depth-sensitive fiber-optic probe," Appl Opt, 47(6): p. 825-34 (Feb. 2008).
Shangguan et al., "Pressure effects on soft tissues monitored by changes in tissue," in Laser-Tissue Interaction IX. Proc SPIE. vol. 3254.p. 366-371 (1998).
Sharwani et al., "Assessment of oral premalignancy using elastic scattering spectroscopy," Oral Oncol, 42(4): p. 343-9 (2006).
Shen et al., "Frequency-estimation-based signal-processing algorithm for white-light optical fiber Fabry-Perot interferometers," Appl Opt, 44(25): p. 5206-14 (Sep. 2005).
Skala et al., "Comparison of physical model and principal component analysis for the diagnosis of normal and neoplastic epithelial tissues in vivo using diffuse reflectance spectroscopy," Optics Express 15(12): 7863-75, (2007).
Skala et al., "An Investigation of Probe Geometry Designs for the Optical Spectroscopic Diagnosis of Epithelial Pre-Cancers and Cancers," Lasers Surg Med, 34(1), 25-38 (2004).

(56) References Cited

OTHER PUBLICATIONS

Subhash et al., "Oral cancer detection using diffuse reflectance spectral ratio R540/R575 of oxygenated hemoglobin bands," J Biomed Opt, 11(1): p. 014018 (Jan./Feb. 2006).

Swartling et al., "Accelerated Monte Carlo Models to Simulate Fluorescence Spectra from Layered Tissues," Journal of Optical Society of America, vol. 20, No. 4, pp. 714-727 (Apr. 2003).

Thueler et al;., "In Vivo Endoscopic Tissue Diagnostics Based on Spectroscopic Absorption, Scattering, and Phase Function Properties," Journal of Biomedical Optics, vol. 8, No. 3, pp. 495-503 (Jul. 2003).

Ti et al., "Effects of probe contact pressure on in vivo optical spectroscopy," Opt Express, 16(6): p. 4250-62 (2008).

Tinet et al., "Fast semianalytical Monte Carlo simulation for time-resolved light propagation in turbid media," J. Opt. Soc. Am. A., vol. 13, No. 9, pp. 1903-1915 (Sep. 1996).

Utzinger et al., "Reflectance spectroscopy for in vivo characterization of ovarian tissue," Lasers Surg Med 28(1): 56-66, (2001).

Utzinger et al., "Fiber optic probes for biomedical optical spectroscopy," J Biomed Opt, 8(1):pp. 121-147 (2003).

de Veld et al., "Autofluorescence and diffuse reflectance spectroscopy for oral oncology," Lasers Surg Med, 36(5): p. 356-64 (2005).

Wang et al., "Targeting spectral signatures of progressively dysplastic stratified epithelia using angularly variable fiber geometry in reflectance Monte Carlo simulations," J Biomed Opt, 12(4): p. 044012 (Jul./Aug. 2007).

Wang et al., 'MCML—Monte Carlo Modeling of Light Transport in Multi-Layered Tissues,' Computer Methods and Programs in Biomedicine, vol. 47, pp. 131-146 (Jul. 1995).

Wang et al., "Monte Carlo Modeling of Light Transport in Multi-Layered Tissues in Standard C," (1992).

Weersink et al., "Noninvasive Measurement of Fluorophore Concentration in Turbid Media with a Simple Fluorescence/Reflectance Ratio Technique," Applied Optics, vol. 40, No. 34, pp. 6389-6395 (Dec. 1, 2001).

Yu et al., "Cost-effective Diffuse Reflectance Spectroscopy Device for Quantifying Tissue Absorption and Scattering in vivo," Journal of Biomedical Optics, vol. 13(6) (Nov./Dec. 2008).

Yu et al., "Diffuse reflectance spectroscopy with a self-calibrating fiber optic probe," Opt Lett, 33(16): p. 1783-85 (2008).

Yu et al., "Tunable-optical-filter-based white-light interferometry for sensing," Opt Lett, 30(12): p. 1452-4 (Jun. 2005).

Yu, "Development of Tunable Optical Filters for Interrrogation of White-Light Interferometric Sensors," in Electrical and Computer Engineering. Virginia Tech: Blacksburg, Virginia (2005).

Yu et al., "Fiber Fabry-Perot sensors for detection of partial discharges in power transformers," Appl Opt, 42(16): p. 3241-50 (Jun. 2003).

Yu et al., "Quasi-Discrete Hankel Transform," Optical Letters, vol. 23, No. 6, pp. 409-411 (Mar. 15, 1998).

Zhang et al., "Innate Cellular Fluorescence Reflects Alterations in Cellular Proliferation," Lasers in Surgery and Medicine, vol. 20, pp. 319-331 (1997).

Zhu et al., "Diagnosis of Breast Cancer Using Diffuse Reflectance Spectroscopy: Comparison of a Monte Carlo Versus Partial Least Squares Analysis Based Feature Extraction Techniques." Lasers in Surgery and Medicine, vol. 38, pp. 714-724 (2006).

Zhu et al., "Use of a Multiseparation Fiber Optic Probe for the Optical Diagnosis of Breast Cancer," Journal of Biomedical Optics, vol. 10, No. 2, pp. 024032-1-024032-13 (Mar./Apr. 2005).

Zhu et al., "Effect of Fiber Optic Probe Geometry on Depth-resolved Fluorescence Measurements from Epithelial Tissues: A Monte Carlo Simulation," Journal of Biomedical Optics, vol. 8, No. 2, p. 237-247 (Apr. 2003).

Zonios et al., "Diffuse Reflectance Spectroscopy of Human Adenomatous Colon Polyps In Vivo," Applied Optics, vol. 38, Issue 31, p. 6628-6637 (Nov. 1, 1999).

Final Office Action for U.S. Appl. No. 12/989,595 (Oct. 3, 2013).

Non-Final Office Action for U.S. Appl. No. 12/680,305 (Aug. 22, 2013).

Extended European Search Report for European Patent Application No. 08833169.9 (Jul. 11, 2013).

Extended European Search Report for European Patent Application No. 09734638.1 (Jul. 3, 2013).

Communication under Rule 71(3) EPC for European Patent Application No. 07753265.3 (Sep. 16, 2014).

Corrected Notice of Allowability for U.S. Appl. No. 12/989,591 (Jul. 17, 2014).

Final Office Action for U.S. Appl. No. 12/680,305 (May 7, 2014).

Notice of Allowance and Fee(s) Due for U.S. Appl. No. 12/989,591 (Feb. 11, 2014).

\* cited by examiner

SMART FIBER OPTIC SENSORS SYSTEMS AND METHODS FOR QUANTITATIVE OPTICAL SPECTROSCOPY

RELATED APPLICATIONS

This application claims the benefit of U.S. Provisional Patent Application Ser. No. 61/266,843, filed Dec. 4, 2009, the disclosure of which is incorporated herein by reference in its entirety.

GOVERNMENT INTEREST

This presently disclosed subject matter was made with U.S. Government support under Grant No. BC044776 awarded by the DOD. Thus, the U.S. Government has certain rights in the presently disclosed subject matter.

TECHNICAL FIELD

The subject matter disclosed herein relates to fiber optic sensors, systems, and methods for quantitative tissue optical spectroscopy. More particularly, the subject matter disclosed herein relates to smart fiber optic sensors, systems, and methods for quantitative tissue optical spectroscopy which can reduce error by combining self-calibration and pressure sensing channels operable concurrently with a specimen sensing channel.

BACKGROUND

Cancer, for example, oral and cervical cancer, is a growing global health problem that disproportionately impacts the developing world. Each year, over 481,000 new cases of oral cancer are diagnosed worldwide, with a 5-year mortality of ~50% and nearly two-thirds of which occur in developing countries. Cervical cancer is the second most common cancer in women with an incidence and death rate of 16 and 9 per 100,000 women, respectively, and 80% of cases occur in the developing world. Detecting and grading precancerous and malignant oral lesions is mostly accomplished by visual screening and biopsy of suspicious tissue sites. The Pap smear is the standard of care for screening for cervical cancer. An effective cancer screening and diagnostic program often requires both sophisticated and expensive medical facilities and well-trained and experienced doctors and nurses. The high death rate in developing countries is largely due to the fact that these countries do not have the appropriate medical infrastructure and resources to support the organized screening and diagnostic programs that are available in the United States or other developed countries. Thus, there is a critical global need for a portable, easy-to-use, low cost, and reliable device that can rapidly screen for oral and cervical cancer in low-resource settings.

It is well documented in numerous studies that oral and cervical cancers, if detected at early stages, have a better chance of being successfully treated with surgery, radiation, chemotherapy, or a combination of the three, therefore significantly improving the survival rates. One such early detection method can include analyzing optical absorption and scattering properties of epithelial tissues which reflect their underlying physiological and morphological properties. UV-visible diffuse reflectance spectroscopy (UV-VIS DRS), which measures tissue absorption and scattering properties, has shown promise for diagnosis of early precancerous changes in the cervix and oral cavity. Tissue absorption and scattering can be quantified using in vivo DRS measurements. For example, in the UV and visible light band, dominant absorbers in oral and cervical tissue are oxygenated and deoxygenated hemoglobin (Hb), arising from blood vessels in the stroma. Light scattering is primarily caused by cell nuclei and organelles in the epithelium and stroma, as well as collagen fibers and cross-links in stroma. Neoplastic and cancerous tissue exhibit significant changes in their physiological and morphological characteristics that can be quantified optically: Stromal layer absorption is expected to increase with angiogenesis, whereas stromal scattering is expected to go down with neoplastic progression as extracellular collagen networks degrade. Epithelial scattering has been shown to increase, for example, due to increased nuclear size, increased DNA content, and hyperchromasia. UV-VIS DRS has a penetration depth that can be tuned to be comparable to the thickness of the epithelial layer or deeper to probe both the epithelial and stromal layers [1], [2], [3].

Hardware employed for UV-VIS DRS measurements typically consists of a broadband light source, a spectrometer for multispectral detection, and a fiber-optic probe for relaying light to and from the instrument. Although fiber-optic probes are well-suited to access tissue sites in the oral cavity and cervix they are susceptible to several sources of systematic and random error that can influence the robustness of this technology, particularly in resource-poor settings. One such error arises from an uncontrolled probe-to-tissue interface which makes it difficult to obtain a reproducible tissue reflectance spectrum due to probe to tissue coupling and physiological changes induced by the probe pressure. That is, a probe technician or operator can unknowingly interfere with spectral measurement of the specimen when contact pressure between the probe and the tissue rises. One study found that there was a decrease in the diffuse reflectance and increase in the scattering coefficient between 400-1800 nm with compression of in vitro human skin [4]. Another study reported that extracted blood vessel radius, oxygen saturation, and Mie theory slope decreased with contact pressure, while the reduced scattering coefficient at 700 nm increased as a function of pressure [5]. A more recent study concluded that elevation in probe pressure can induce major alterations in the profile of the reflectance spectra between 400-650 nm and the changes in the extracted tissue optical properties depend not only on the probe pressure, but also on tissue type [6]. It is generally believed that the changes may be attributed to the compression of the blood vessels which causes reduced blood flow and alterations in the metabolism of the tissue as well as a change in the density of the scatterers. Thus, it appears that unknown and uncontrolled contact pressure at the probe specimen interface can adversely affect measurements and early detection of affected tissue.

Another error in conventional systems can arise from the lack of a robust, real-time calibration makes the calibration process time-consuming and potentially inaccurate, particularly when attempting to quantify absolute absorption and scattering coefficients. It has been established that in order to consistently yield accurate estimation of tissue optical properties, calibration can compensate for the wavelength-dependent instrument response, lamp intensity fluctuations, and fiber bending losses [7], [8]. Conventional calibration techniques typically rely on measurements using reflectance standards of known optical properties and/or tissue phantoms, typically after the clinical measurements are completed. These measurements are subject to a number of limitations, however. First, because the calibration is performed at the beginning or end of the study, real-time instrument fluctuations, such as lamp drift and fiber bending loss cannot be compensated for. Second, these measurements can require an additional thirty minutes for lamp warm-up and another ten to twenty minutes for calibration, which adds up to a significant amount of time, especially in a clinical setting. Thus, a better calibration method is needed, on that can compensate for real-time instrument fluctuations.

Finally, and in addition to being problematic and error prone, typical DRS systems can be expensive to use as they comprise bulky, high power and expensive optical components, such as thermal light sources, spectrometers, and cooled CCD cameras, which need a stable power supply. Thermal light sources have large footprint, short life-time, low power efficiency, and low coupling efficiency to optical fibers. Spectrometers using grating spectrometers and cooled CCD cameras have extremely high wavelength resolution and sensitivity, but are very bulky and expensive and consume a large amount of electrical power. In addition, a stable power supply is very often required to operate a thermal lamp and a CCD camera. Taken together, it is very difficult for DRS systems in their current forms to be directly used for cancer screening in developing countries.

Consequently, there remains a need for improved smart fiber optic sensor systems and methods for quantitative tissue optical spectroscopy that overcome or alleviate shortcomings of the prior art systems and methods. In particular, there remains a need for a low power consumption, low-cost DRS device that can be used to obtain accurate and reproducible quantitative measurements of absorption and scattering coefficients with applications to global health screening of cervical and oral cancers. Such improvements can comprise, but are not limited to, utilizing of emitting diodes (LEDs) as illumination sources; using miniature fiber-optic spectrometers for light detection and a smart fiber-optic probe for reliable measurements of tissue diffuse reflectance spectra. The LEDs and spectrometers can be powered and controlled by a laptop computer using custom computer readable media, making the system highly portable. Smart fiber optic sensors, systems, and methods can integrate a specimen sensing channel, a self-calibration channel, and an interferometric fiber-optic pressure sensor into a single instrument. The pressure sensor can provide real-time pressure readings at the probe-specimen interface such that an operator can adjust the applied force on the probe. The spectra can only be saved and processed if the desired pressure is reached. The pressure sensor can ensure that the probe-tissue coupling is reliable and the pressure induced tissue physiological changes are consistent between measurements. The self-calibration channel can collect a calibration spectrum concurrently with the tissue spectrum, which will be used to correct for source fluctuations and fiber bending loss that occurs during the measurements. With the smart fiber optic sensors, systems, and methods disclosed herein it can be possible to perform accurate and reproducible DRS for rapid screening of cancers or charactering in vivo tissues in resource-limited countries without having to use expensive optical components and high capacity stable power supplies. More importantly, it can eliminate the need for instrument warm-up and extra on-site calibration measurements, thus saving 40-60 minutes of time.

SUMMARY

The subject matter described herein includes relates to smart fiber optic sensors, systems, and methods for quantitative tissue optical spectroscopy. According to one aspect, a smart fiber optic sensor comprises a sensing channel for illuminating a specimen and for collecting spectral reflections from the specimen from which specimen spectral data can be determined. Smart fiber optic sensor can comprise a pressure sensing channel for collecting pressure sensor spectral reflections from which a contact pressure can be determined and a calibration channel for obtaining calibration spectral reflections usable for correcting the specimen spectral data.

A smart fiber optic sensor system can comprise a smart fiber optic sensor described above and a signal processor or processing unit, coupled to the each of the sensing channel, the pressure sensing channel, and the calibration channel, the processing unit being adapted to receive and correct the spectral data of the specimen and for calculating the contact pressure at the sensor/specimen interface in real-time.

A method for utilizing a smart fiber optic sensor can comprise contacting the specimen with the smart fiber optic sensor, generating specimen spectral data, pressure sensor spectral data, and calibration data. The method can further comprise calculating contact pressure using the pressure sensor spectral data and correcting specimen spectral data using the calibration data. The specimen spectral data can optionally be analyzed and stored.

At least portion of the subject matter described herein may be implemented in hardware, a combination of hardware and software, firmware, or any combination of hardware, software, and firmware. As such, the terms "function" or "module" as used herein refer to hardware, a combination of hardware and software, firmware, or any combination of hardware, software, and firmware for implementing the features described herein. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be described with reference to the accompanying drawings, of which.

DETAILED DESCRIPTION

Figure 1:
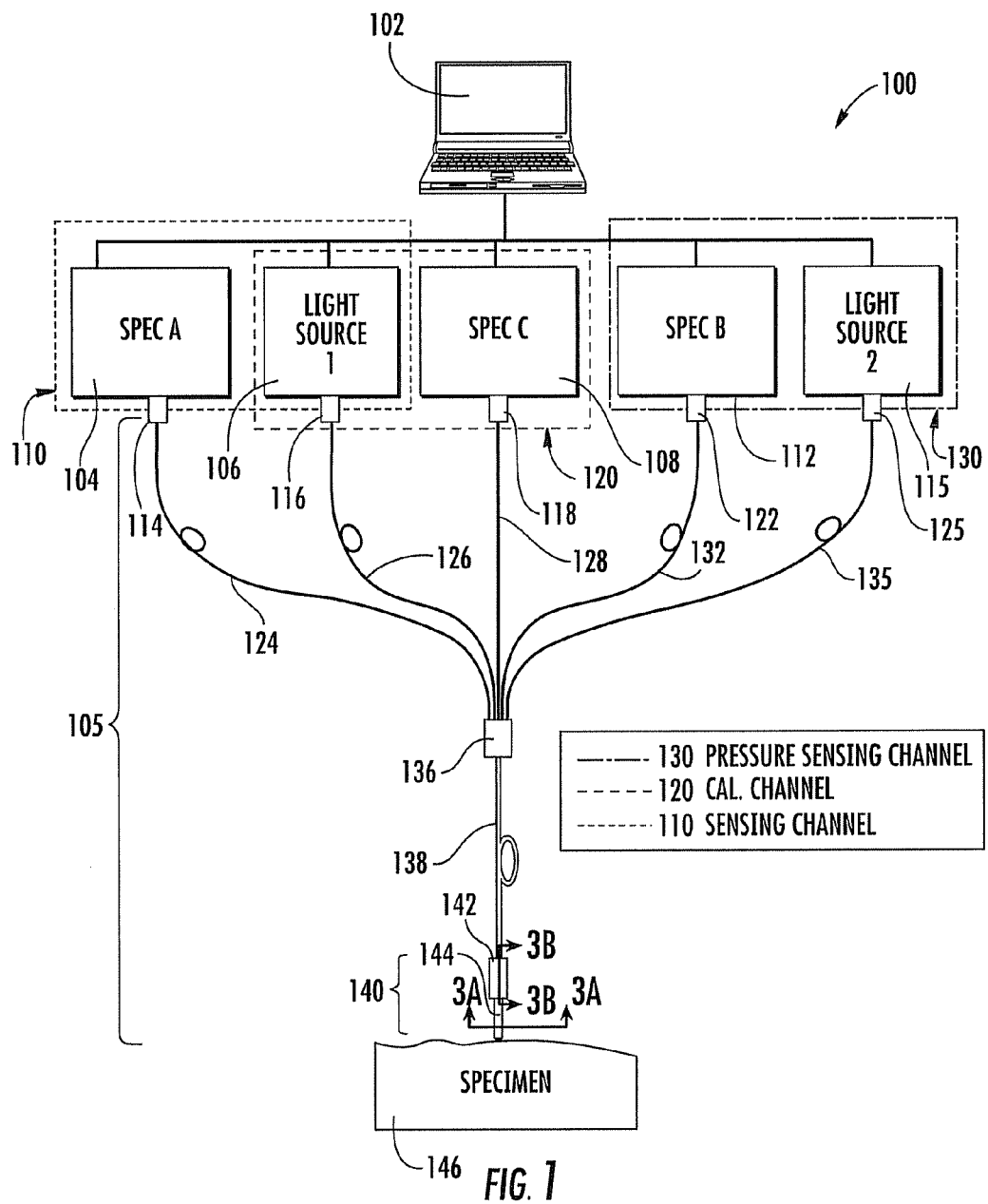
FIG. 1 is a block diagram of an optical spectroscopy system that utilizes smart fiber optic sensors according to an embodiment of the subject matter disclosed herein.

The subject matter described herein comprises smart fiber optic sensors, systems, and methods for quantitative tissue optical spectroscopy. In one embodiment, the system can include a smart fiber optic sensor comprising a specimen sensing channel, a self-calibrating channel, and a pressure sensing channel each of which can operate concurrently and in real-time to ensure reliable measurements. The systems and methods disclosed herein can determine whether to analyze and store generated data from a specimen based upon pressure detected using the smart fiber optic sensor. The present disclosure can be described by the embodiments given below. It is understood, however, that the embodiments discussed herein are not necessarily limitations to the present disclosure, but can be used to implement the subject matter disclosed herein. Having summarized various aspects of the present subject matter above, reference will now be made in detail to describe the subject matter as illustrated in the drawings. While the subject matter herein can be described in connection with these drawings, there is no intent to limit it to the embodiment or embodiments disclosed therein. On the contrary, it can be appreciated from the description provided herein that a variety of alternative embodiments and implementations may be realized. It can further be understood that various details of the subject matter described herein may be changed without departing from the scope of the subject matter described herein. Wherever possible, the same reference numbers will be used throughout the drawings to refer to the same or like parts.

As illustrated in the figures submitted herewith, some sizes of structures or portions may be exaggerated relative to other structures or portions for illustrative purposes and, thus, are provided to illustrate the general structures of the present subject matter. Furthermore, relative terms such as "upper," "lower," "top," "bottom," "on" or "above" may be used herein to describe one structure's or portion's relationship to another structure or portion as illustrated in the figures. It will be understood that relative terms such as "upper," "lower," "top," "bottom," "on" or "above" are intended to encompass different orientations of the apparatus in addition to the orientation depicted in the figures. For example, if the apparatus in the figures is turned over, structure or portion described as "above" other structures or portions would now be oriented "below" the other structures or portions. Likewise, if the apparatus in the figures is rotated along an axis, stricture or portion described as "above", other structures or portions would now be oriented "next to" or "left of" the other structures or portions.

Referring now to FIG. 1, one embodiment of a smart fiber optic sensor system, generally designated 100, is disclosed. In one embodiment, system 100 comprises a diffuse reflectance spectroscopy (DRS) system. Smart fiber optic sensor system 100 can be used to perform noninvasive UV-Vis-NIR diffuse reflectance as well fluorescence spectroscopy in clinical settings or preclinical animal models. The system can comprise one or more LEDs as illumination sources, a three-channel miniature spectrometer for light detection, a fiber-optic probe, and a processing unit or module for processing custom computer readable media. Smart fiber optic sensor system 100 can further integrate a diaphragm-based Fabry-Perot interferometric (DFPI) pressure sensor with a tissue sensing channel. As FIG. 1 illustrates, smart fiber optic system 100 can comprise a processor or processing unit 102 connected to each of three fiber optic groupings or "channels" and a smart fiber optic probe, or sensor, generally designated 105. Processing unit 102 can comprise a portable laptop computer. Each channel can comprise fiber optic groupings or "legs" distributed between illumination sources and imaging spectrometer and/or spectrometer channels A, B, and C. One or more of the fiber optic channels can share an illumination source and/or an imaging spectrometer or spectrometer channel.

A first fiber optic channel 110 can comprise a sensing channel 110 wherein the illumination source comprises a first light source 106 and a first spectrometer channel A, designated 104. A second fiber optic channel 120 can comprise a calibration channel wherein the illumination source comprises first light source 106 and a second spectrometer channel C, designated 108. Thus, both sensing channel 110 and calibration channel 120 can share first light source 106. Optionally, calibration channel 120 can utilize a same spectrometer and/or spectrometer channel as either sensing channel 110 or a fiber optic pressure sensor channel. A third fiber optic channel 130 can comprise a fiber optic pressure sensor channel wherein the illumination source can comprise a second light source 115 and a third spectrometer channel B, designated 112. The reflectance and/or fluorescence spectrum from the specimen can be detected by spectrometer channel 104, the signals from a pressure sensor can be detected by spectrometer channel 112, and the calibration spectrum can be detected by spectrometer channel 108. In an alternative embodiment, three separate spectrometers can be used rather than a three-channel spectrometer. In another alternative embodiment, a dual-channel spectrometer can be used instead of a three-channel spectrometer. For example, spectrometer could comprise a dual channel fiber-optic spectrometer such as those manufactured by Avantes BV, wherein one channel could detect DRS from sensing channel and the second spectrometer channel could be shared by calibration channel 120 and pressure sensing channel 130. That is, the second channel of a dual channel spectrometer could detect the signals from calibration channel and pressure sensor. In one embodiment, spectrometer can comprise a white LED based miniature spectrometer consisting of a high power white LED and a USB 4000 spectrometer, such as those manufactured by Ocean Optics of Orlando, Fla. The spectrometer can comprise a 1-mm fiber optic for illumination and another 1-mm fiber for collection with a source-to-detector separation (SDS) of 2.3 mm. Diffuse reflectance from a specimen can be detected by spectrometer channel 104.

In one embodiment, fiber optic pressure sensor channel 130 can comprise an interferometric pressure sensor. Pressure sensor channel 130 can provide real-time pressure data at the probe-specimen interface such that an operator, or technician can manually control the pressure at the interface within an optimal minimal range for ensuring best probe-specimen coupling, without affecting the tissue physiology. Thus, the smart fiber optic sensor 105 disclosed herein can integrate together the sensing 110, calibration 120 and, for example, interferometric pressure sensor channels 130 into a single optical probe. Smart fiber optic sensor 105 can be adapted to accommodate any probe instrument, including but not limited to, side firing and forward firing probes.

Sensing channel 110 can comprise a detection fiber portion, or collection leg 124 which can couple to first spectrometer 104 at coupler 114. Sensing channel 110 can also comprise an illumination fiber leg 126 coupled to first light source 106 at coupler 116 for collecting a DRS from a specimen. In one embodiment, specimen can comprise an in vivo tissue sample 146. In one embodiment, first light source 106 can comprise a white light emitting diode (LED) such as white fiber LED LE-1x-c manufactured by WT&T Inc. Light source 106 can comprise a wavelength range from 400 to 700 nm as the source for DRS. In one embodiment, sensing channel 110 can comprise a high power white LED as the source for DRS and/or one or multiple UV/visible LEDs (with or without a bandpass filter) as the excitation source for fluorescence spectroscopy. The white LED and color LED(s) can share the same source fibers (152, FIG. 2) or have independent source fibers. The fluorescence channel can be used to quantify both intrinsic fluorophores (such as FAD, NADH, collagen and porphyrin), and endogenous fluorophores (such as the nanoparticle contrast agents, chemotherapy drug, and Doxirubicin). The different LEDs can be switched on/off sequentially. In other embodiments, first light source 106 can comprise any suitable broadband light source. In one embodiment, a broadband light source with a monochromator (e.g., a scanning double-excitation monochromator) or a plurality of laser diodes may also be used along with a plurality of photodetectors in lieu of spectrometer 104. It is well established that LEDs utilize less power and/or energy than conventional illumination sources such as xenon lamps or white light bulbs.

Figure 3A:
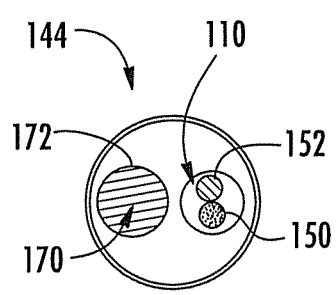
FIGS. 3A and 3B illustrate cross-sectional views of an embodiment of smart fiber optic sensors according to the subject matter disclosed herein.
Figure 3B:
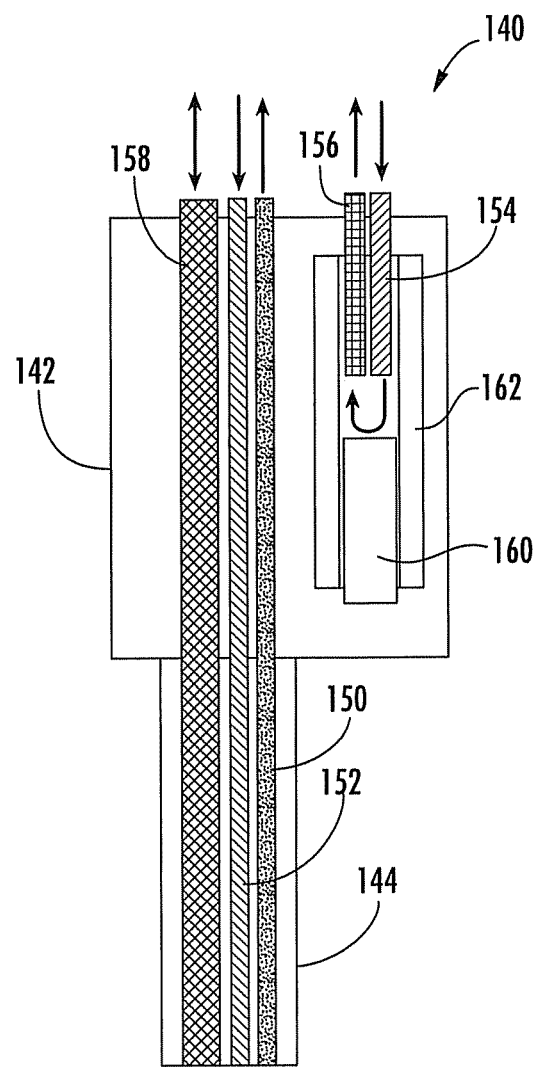

Sensing channel 110 can comprise a channel wherein light from first light source 106 illuminates a sample, or specimen 146 and at least one detection fiber 150 can capture the reflected light (i.e., spectral data) which can ultimately be provided to spectrograph 104 via the fiber array shown in cross-sectional views of FIGS. 3A and 4. The cross-sectional views are associated with the open ended terminus of probe tip 144 (FIG. 3B). Notably, each individual detection fiber 150 can run the entire length of collection leg 124 and main portion of probe 138.

Still referring to FIG. 1, calibration channel 120 can comprise illumination fiber leg 126 and a calibration return leg 128. Calibration return leg 128 can couple to second spectrometer 108 at coupler 118. Illumination fiber leg 126 can share first light source 106 with sensing channel 110, for example, a white LED, and can collect a calibration spectrum concurrently with the tissue measurement which can be used for real-time instrument and probe calibration. Illumination fiber leg can comprise two source fibers, for example illumination source fiber 152 utilized in sensing channel 110 for illuminating the specimen and a calibration source fiber 154 utilized in calibration channel 120 for internal calibration (see FIG. 2B). Illumination source fiber 152 and calibration source fiber 154, respectively, can run parallel to each other within illumination fiber leg 126. Illumination source fiber 152 can extend into a ridged probe tip 144 for contacting and sensing the specimen. In one embodiment, each of illumination source fiber 152 and calibration source fiber 154 can comprise the same diameter fiber or fibers and all of the fibers can be made from the same materials (e.g., same fiber clad, core, etc.) and can comprise the same numerical aperture (NA) for identical bending response. Calibration source fiber 154 is discussed below with respect to FIG. 3B, but may not extend all the way to specimen surface 146. Calibration return leg 128 of calibration channel 120 is also discussed with respect to FIG. 3B and can be useful for collecting calibration light generated at first light source 106 and reflected by a reflective material 160 (FIG. 3B) and transmit the reflected light to spectrometer 108. In one embodiment, smart fiber optic sensor 105 can be used to concurrently measure the spectral data of first light source 106 and spectral data of sample 146. Notably, the configuration is advantageous because it can account for real-time light source intensity fluctuations and fiber bending loss (i.e., light intensity fluctuations caused by bending the instrument). For example, the bending effect on illumination source fiber 152 is assumed to be the same as that of calibration source fiber 154. Also, light source warm-up and separate calibration measurements are also unnecessary with a smart fiber optic sensor and system.

Still referring to FIG. 1, fiber optic pressure sensor channel 130 can comprise second illumination fiber leg 135 and a pressure return leg 132. Second illumination fiber leg 135 can couple to second light source 115 at second light source coupler 125. Pressure return leg 132 can couple to spectrometer 112 at spectrometer coupler 122. Second illumination fiber leg 135 and pressure return leg 132 can comprise a single lead in/out fiber (single-mode or multi-mode) forming a low-coherence DFPI at the end face of the lead in/out fiber. Second light source 115 can comprise an 850 nm LED with a spectral width of 30 or 60 nm such as those manufactured by Appointech Inc. Smart fiber optic sensor 105 can comprise collection, illumination fiber, second illumination fiber, calibration return, and pressure return legs. Smart fiber optic sensor 105 can further comprise a probe portion, leg 138 extending from a breakout tube 136. Probe portion can comprise a probe tip portion, generally designated 140. Probe tip portion 140 can comprise a calibration housing portion 142 and a rigid probe tip 144. Probe tip 144 can contact a surface of specimen 146. Specimen 146 can comprise a tissue sample or any turbid medium. A contact pressure at the probe/specimen interface can advantageously be calculated and controlled using fiber optic pressure sensing channel 130.

Figure 2:
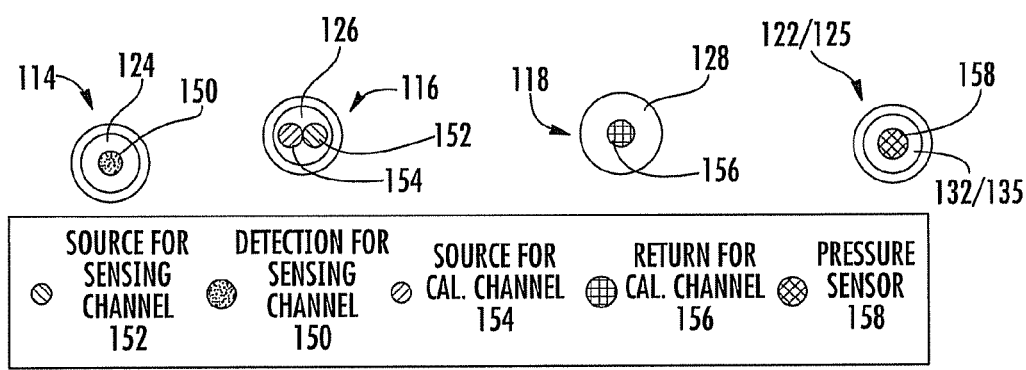
FIG. 2 illustrates source and detection fiber optics for use with optical spectroscopy systems and methods disclosed herein.

FIG. 2 illustrates various source and collection fibers for use in smart fiber optic sensor system 100. Source and collection fibers can traverse various legs of the smart fiber optic system 100 described in FIG. 1. In one embodiment, sensing channel 110 comprises at least one illumination source fiber 152 that traverses illumination fiber leg 126 and at least one collection fiber 150 that traverses collection leg 124. Each of illumination source fiber 152 and collection fiber 150 traverse the entire length of probe leg 138 and extend through probe tip 144 and can be polished flush with a distal end of probe tip 144. FIG. 2 illustrates collection fiber 150 which connects to spectrometer 104 at coupler 114. In one embodiment, calibration channel 120 comprises at least one calibration source fiber 154 and at least one calibration return fiber 156. FIG. 2 also illustrates illumination source fiber 152 of sensing channel 110 and calibration source fiber 154 of calibration channel 120 each of which traverse illumination fiber leg 126 and connect to first light source 106 at coupler 116. Calibration source fiber 154 can traverse probe leg 138 and loop back or terminate in calibration housing portion 142 of probe tip portion 140. In one aspect, illumination source fiber 152 comprises a 400/400/480 µm fiber for illumination. Calibration source fiber 154 can comprise another fiber of the same diameter for calibration. Illumination source fiber 152 can provide a sensing depth sufficient to probe both the epithelium and stroma within a tissue sample. These dimensions are not limiting as any suitable fiber diameter can be used for illumination source fiber 152 and/or calibration source fiber 152. It is also contemplated that the fibers can be suitably sized and/or shaped to comprise a variable sensing depth by using either multi-separation probe or angled probe designs. Please note that illumination fiber leg 126 can comprise any suitable number of calibration source fibers 154 and illumination source fibers 152, and is not limited to the size/shape/ or quantity illustrated.

FIG. 2 also illustrates at least one calibration return fiber 156 that comprises reflected light traversing probe leg 138 calibration return leg 128 to ultimately connect to spectrometer 108 at coupler 118. Together, calibration source fiber 154 and calibration return fiber 156 can form calibration channel 120. FIG. 2 also illustrates a lead in/out fiber 158 comprising a pressure sensor fiber traversing each of second illumination fiber leg 132, pressure return leg 135, and probe leg 138. In one embodiment, pressure sensor channel 130 comprises second illumination fiber leg 132 and pressure return leg 135 wherein lead in/out fiber 158 can be disposed in each leg. The various legs can comprise any suitable material for housing one or more fiber optics. For example, legs can comprise stainless steel, or metallic tubes which include bored holes for placement of fiber optic fibers. In another embodiment, legs can comprise hollow tubes where a filling material is injected or disposed which can surround the respective fiber optic fibers.

FIGS. 3A, 3B, and 4 illustrate various cross-sectional views of probe tip 144 and calibration housing portion 142. In one aspect, probe tip can comprise ridged elements (not shown) to provide stability and/or interfacing capability for smart fiber optic sensor 105. FIG. 3A illustrates one embodiment of a cross-sectional view of probe tip 144 as it appears from a distal end for contacting specimen. FIG. 3A illustrates a cross-sectional view of probe portion 144, wherein illumination source fiber 152 and collection fiber 150 are disposed having longitudinal axes parallel to a longitudinal axis of fiber optic pressure sensor, generally designated 170. The illumination source fiber 152, collection fiber 150, and diaphragm 172 of pressure sensor 170 can be polished to the same plane such that each can be flush with a specimen surface during spectroscopic measurement. Probe tip 144 can comprise a stainless steel tube which surrounds illumination source fiber 152, collection fiber 150, and pressure sensing in/out fiber 158.

FIG. 3B illustrates an exemplary smart fiber optic sensor tip portion 140 including includes the calibration housing 142 for the self-calibration optical fibers and probe tip 144. In one embodiment, probe tip portion 140 receives both illumination source fiber 152 and calibration source fiber 154 from illumination fiber leg 126. As shown in FIG. 3B, illumination source fiber 152 passes completely through housing section 142 in order to interface with a specimen 146 (FIG. 1). Calibration source fiber 154, however, terminates within housing section 142. In one embodiment, light exits calibration source fiber 154 and is directed to a reflective material 160. Reflective material 160 may include a mirror, a polished metal element (e.g., a polished metal wire), a reflective rod, and/or any suitable reflective material known now or in the future. In one aspect, reflector material can comprise any shape and/or material. In one embodiment, a calibration source 154 and return 156 fiber can be inserted into a sealed tube filled with diffusely reflective powers such as a Spectralon® reflectance material manufactured by Labsphere. After reaching reflective material 160, light can be reflected towards a calibration return fiber 156. The reflected light can then be received and carried by calibration return fiber 156 to spectrometer, or spectrometer channel 108. A flexible stainless steel tube 162 can surround calibration source 154 and return 156 fibers.

In one embodiment, calibration source fiber 154 and calibration return fiber 156 can comprise the same fiber (i.e., a source/return calibration fiber). For example, a single source-return calibration fiber may originate from light source 106, enter housing section 142, and bend or loop back in such a manner that the calibration source/return fiber exits housing section 142. That is, the calibration source-return fiber can be bent within housing section 142 in the smart fiber optic sensor such that the calibration source fiber functions as the calibration return fiber (since a mirror or other reflective element is not used). The calibration fiber would then be configured to interface with spectrometer channel 108 via calibration return leg 128. Notably, reflective material 160 would not be utilized in this particular embodiment. Although cross sectional view shows one calibration return fiber 156, additional calibration return fibers may be used. For example, additional calibration return fibers may be implemented as backup return fibers in case the primary return fiber fails or if additional calibration channels are to be implemented.

In one embodiment, smart fiber optic sensor 105 can comprise calibration channel that can be used to record the lamp spectrum and instrument/fiber responses concurrently with tissue measurements. For example, at least one calibration source fiber 154 can transmit, or communicate calibration light and calibration return fiber 156 can collect, or communicate the calibration light reflected by reflective material 160 within calibration housing 142 and transmit it to spectrometer 108. The calibration spectra from the calibration channel can be detected by spectrometer 108 and used for calibration of the specimen spectrum obtained concurrently.

In one embodiment, calibration source fiber 154 of the calibration channel can have the same diameter as and run along the illumination fiber 152 of the sensing channel. Calibration return fiber 156 can be the same diameter as the collection fiber 150 in the tissue channel for identical bending response. To account for the wavelength dependence, a correlation factor may be applied before being processed with the specimen spectral data. For example, because the calibration channel may have wavelength responses that differ from the wavelength responses exhibited in the sensing channel, the wavelength response in the calibration channel may require correction and/or compensation. For example, to correct the calibration channel's wavelength dependence, a spectral measurement may be taken from a reflectance standard (e.g., a Spectralon puck), which is characterized by a flat wavelength response. A correction factor may be generated for each sensor, or probe by dividing the spectral data of the reflectance standard by the self-calibration spectrum concurrently obtained with spectral data of the reflectance standard. For example, the correlation factor may comprise $$F_{corr}(\lambda) = \text{Puck}(\lambda) / SC_{puck}(\lambda)$$

where Puck (A) is measured from Spectralon puck by the sensing channel and $SC_{puck}$ (A) is the concurrent spectrum measured by the calibration channel. The calibrated reference phantom and tissue spectra can be input into the fast scalable Monte Carlo inverse model [9] which extracts the tissue $\mu_s'$ and $\mu_s$, from which tissue absorber concentrations can be derived. With the smart fiber optic sensor, or probe, no separate calibration measurements are needed. Exemplary Monte Carlo algorithms suitable for use with the subject matter described herein can be found, for example, in international patent application number PCT/US2007/006624 to Palmer et al.; international patent application number PCT/US2008/0270091 to Ramanujam et al.; and U.S. Pat. No. 7,835,786 to Palmer et al., the entireties of which are hereby incorporated by reference herein. In an alternative, a diffusion algorithm or inverse diffusion algorithm may be used instead of a Monte Carlo algorithm. Notably, tissue measurements can be started right after the instrument is turned on and fiber bending loss can be accounted for in real-time. All these together could save as much as 60 minutes of precious time.

Figure 4A:
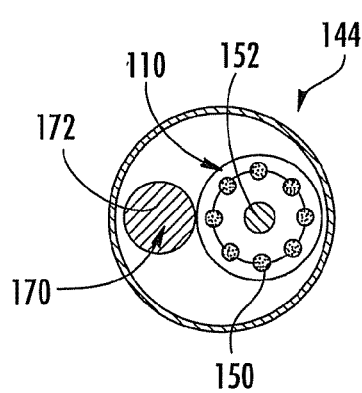
FIGS. 4A and 4B illustrate cross-sectional views of an embodiment of smart fiber optic sensor according to the subject matter disclosed herein.
Figure 4B:
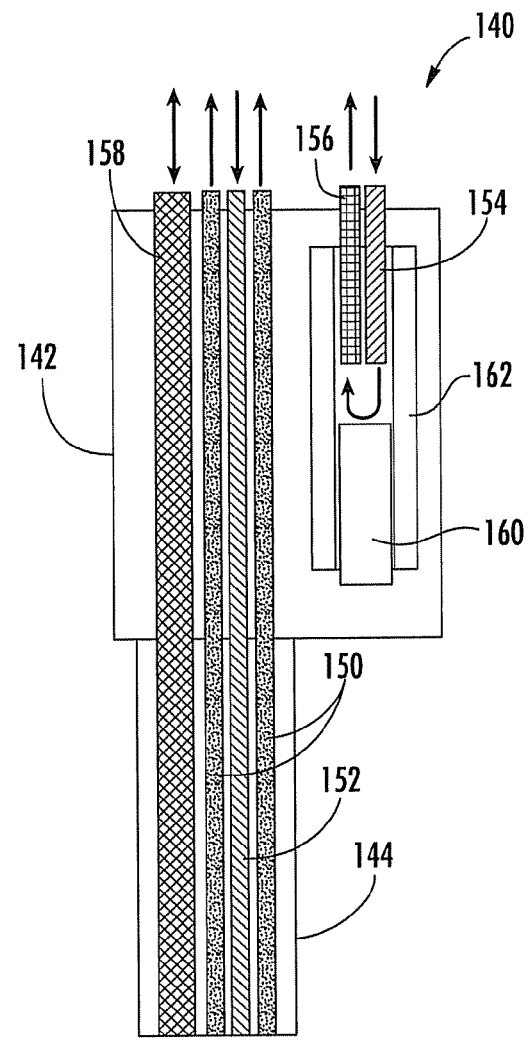

FIGS. 4A and 4B illustrate another cross-sectional embodiment of probe tip 144 which could be used as an alternative to that shown in FIG. 3A. If used, FIG. 3B cross-section would adjust accordingly to account for the arrangement of one or more detection, or collection fibers 150 about source fiber 152 as illustrated in FIG. 4B. FIG. 4A illustrates illumination source fiber 152 coupled to light source 106 substantially disposed in the center of eight collection fibers 150 coupled to spectrograph 104 to collect the diffusely reflected light from specimen at one or more wavelengths. In one embodiment, eight detection fibers 150 can be 200 μm in diameter. In one embodiment, probe tip 144 can be 9.3 cm long having a diameter of 2.1 mm and can fit within the lumen of a 14 gage biopsy needle cannula. For illustration purposes, the embodiments of the cross-sectional view of probe tip 144 are shown by FIGS. 3A and 4, however, it is noted that any suitable arrangement and/or number of source and collection fibers can be used. For example, the illumination core may include a plurality of smaller illumination fibers (i.e. instead of one single illumination source fiber 152) to obtain an illumination core diameter that maximizes both the coupling efficiency for the light source and the signal-to-noise ratio (SNR) for fluorescence measurements (if applicable). In one embodiment, illumination source fiber 152 can be used to emit light on a tissue sample (e.g., specimen 146. FIG. 1) to be examined. Light can be generated by first light source 106 and provided directly to illumination fiber leg 126 of smart fiber optic sensor 105 or via a monochromator (not shown). Notably, light carried by illumination source fiber 152 and calibration source fiber 154 can be characterized by the same spectral data.

Figure 5:
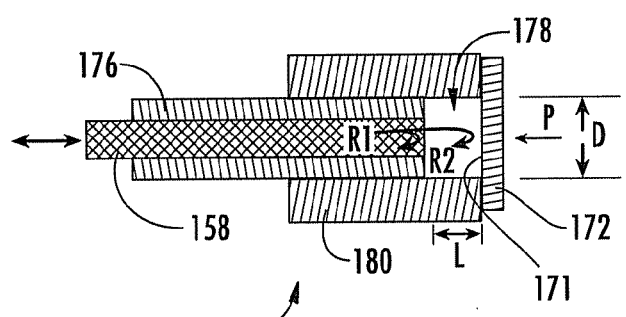
FIG. 5 illustrates an embodiment of a fiber optic pressure sensor for use with the systems and methods disclosed herein.

FIG. 5 illustrates a fiber optic pressure sensor, generally designated 170. In one embodiment, pressure sensor 170 can comprise a DFPI sensor formed at a cleaved end face of lead in/out fiber 158. Details regarding DFPI sensor interrogation can be found in references [10] and [11], the entireties of which are incorporated by reference herein. Pressure sensor 170 can be illuminated by an 850 nm (or any other near infrared (NIR) wavelengths) LED with a spectral width over 30 or 60 nm. The 850 nm LED can be on during all spectroscopic measurements and the spectral output of spectrometer channel 115 can be processed immediately to calculate the pressure at the probe-tissue interface. Lead in/out fiber 168 can be disposed within a ferrule 176 and tube 180. In one embodiment, ferrule 176 can comprise a fused silica ferrule and tube 180 can comprise a fused silica tube. Any suitable materials can be used however. A high temperature epoxy or a high power laser can bond fiber 168, ferrule 176, tube 178, and diaphragm 172 together. A static or dynamic external pressure P can be applied on the outer side of the diaphragm 172 and deflect the diaphragm towards the fiber tip 158, reducing the length of an air cavity 178. The extremely low thermal expansion coefficient of fused silica made the cavity length L highly insensitive to environmental temperature change. Outer diameter D of pressure sensor 170 can comprise a range from 3 to 5 mm. Length L of air cavity can be measured using low-coherence interferometry. In general, light from second light source 115 can be launched into the sensor head using the lead in/out fiber 158. The low-coherence light can propagate into air cavity 178, where the beam can be partially reflected by the end face of fiber 158 as illustrated by R1, and at least partially reflected at an inner surface 171 of diaphragm 172 as illustrated by R2. The reflected beams R1 and R2 can propagate back to a detector or spectrometer 112 through the lead in/out fiber 158 and interfere with each other. By analyzing an interferogram, the cavity length can be calculated in real-time with nm to sub-nm accuracy. External pressure P (e.g., contact pressure at sensor-specimen interface) applied on the outer surface can bend the diaphragm 172 toward the fiber 158 and thus changes the length of air cavity 178. The applied pressure, or force can be calculated by measuring the change of the cavity length from atmospheric pressure. Reflected beams R1 and R2 can comprise reflectance data and/or pressure sensor spectral data. Pressure sensor 170 can operated within a linear region (a small region on one side of an interference fringe near its quadrature point) for best sensitivity and largest signal bandwidth, which is required for detection of dynamic pressure waves. DFPI sensors can comprise a sensitivity of 87 mV/psi and a high resolution of 0.023 psi (or 159 Pa) and a dynamic range over 100 psi [11] [12].

Still referring to FIG. 5, pressure sensor 170 can be fabricated in one embodiment by inserting a 50/125 μm multimode fiber into a fused silica ferrule having an outer diameter of 1.5 mm and inner diameter of 127 μm. The fiber can be bonded to a ferrule using high temperature epoxy and the tip of the fiber can be polished down to the ferrule with optical quality. A 100 μm thick fused silica diaphragm can be bonded to the polished end face of a 1.0 cm long fused silica outer tube with a 1.5 mm inner diameter. The ferrule with fiber can be inserted into the outer tube at the end without the diaphragm until a cavity length of 10-14 μm can be measured by an interrogation instrument. The ferrule and the outer tube can be permanently bonded together with high temperature epoxy and the air cavity length can be monitored and adjusted during a curing process. The diaphragm can be polished (with the probe tip 144) down to close to 50 μm.

Figure 6:
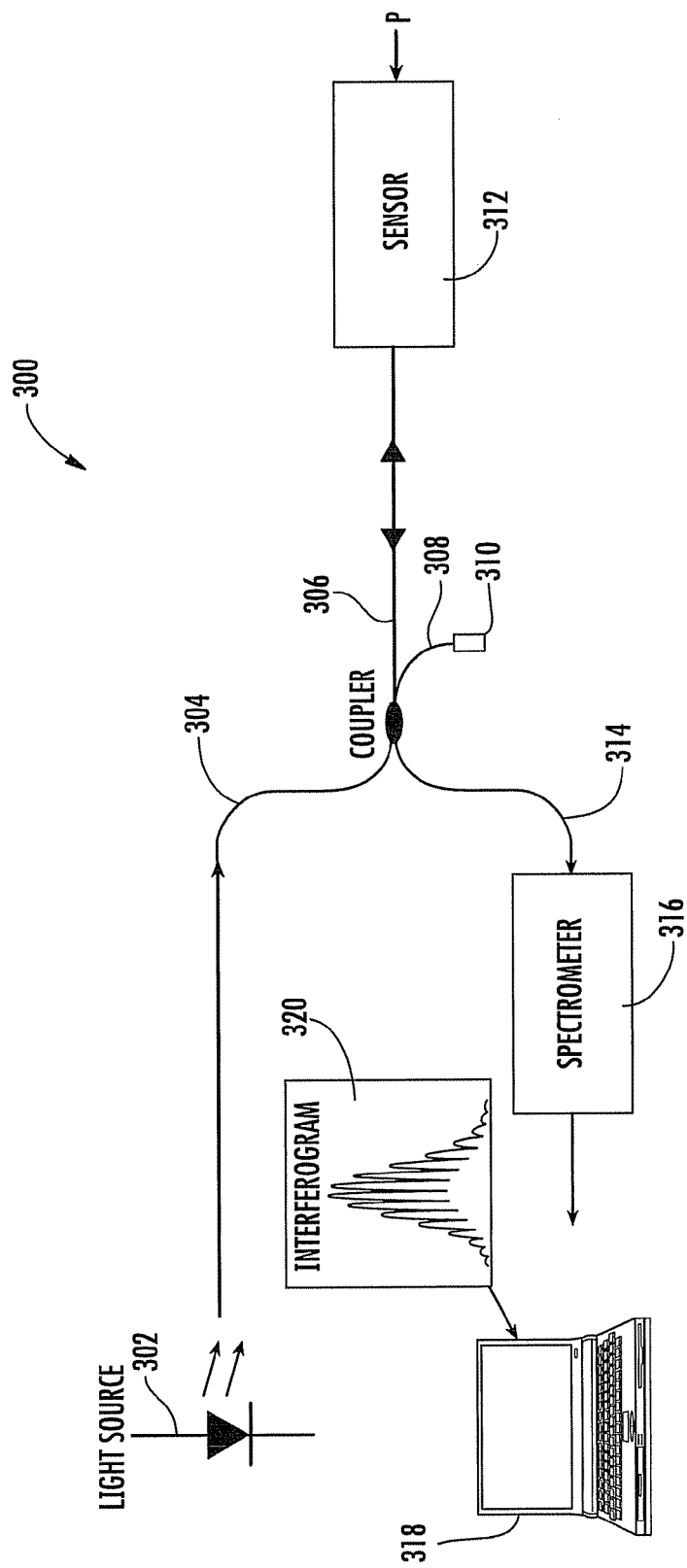
FIG. 6 is a block diagram of a fiber optic pressure sensor system for use with optical spectroscopy systems and methods disclosed herein.

FIG. 6 illustrates a block diagram of an embodiment of pressure sensing channel, generally designated 300. Pressure sensing channel 300 can illustrate components essentially corresponding to pressure sensing channel 130 of FIG. 1. The real-time probe pressure can be displayed on a processing unit, such as portable laptop computer 318 so that an operator can adjust the force applied to the probe. Programming can be used such that if and only if the desired pressure is reached during a scan, will the specimen spectra be saved and processed. A light source 302 can generate a low-coherence light source. Light source 302 can comprise an 850 nm LED with 30 or 60 nm spectral widths and traverse an illumination leg 304. A multimode fiber coupler can be used to couple a sensor head 312 to light source 302 and sensor head 312 to spectrometer 316. For example a pressure sensing leg 306 can be coupled at coupler to send a signal to spectrometer 316 over return leg 314 upon receiving and reflecting low-coherence light from light source 302. An inactive portion of sensing leg 308 can be placed in an index matched terminal 310 as to not interfere with the light and/or signal of pressure sensing leg 306. Sensor head 312 can comprise pressure sensor 170 discussed above, and can optionally comprise a DFPI sensor head. A probe pressure range of 0-15 psi can be selected. For best measurement consistency, a pressure resolution of 0.1 psi can be selected. The sensitivity of the DFPI sensor under an external force or contact pressure difference δ can be expressed as:

$$\delta = y_0(P)/P = 1.74 \times 10^{-5} a^4/h^3 \text{ (nm/psi)}$$

where $y_0$ (nm) is the deflection of the diaphragm at the center, $a = D/2$ (μm) is the effective radius of diaphragm 172 (FIG. 5) and h (μm) is the thickness of diaphragm 172. The sensitivity as a function of the diaphragm thickness at three diaphragm diameters (D=1.0, 1.5 and 2.0 mm) is plotted in FIG. 8. An interferogram 320 of signal sent over return leg 314 can be analyzed using a simple fringe peak tracking algorithm or function. In one embodiment, a measured cavity length of a DFPI sensor showed a ±0.5 nm stability over 48 hours with a dynamic range over ten microns and ±1.5-nm shift in the temperature range of 10 to 45° C. When a diaphragm of 1.5 mm effective diameter and a thickness of 50 μm can be selected, a sensitivity of 44 nm/psi, and thus a pressure resolution of 0.068 psi can be easily achieved within 10-45° C.

Figure 7A:
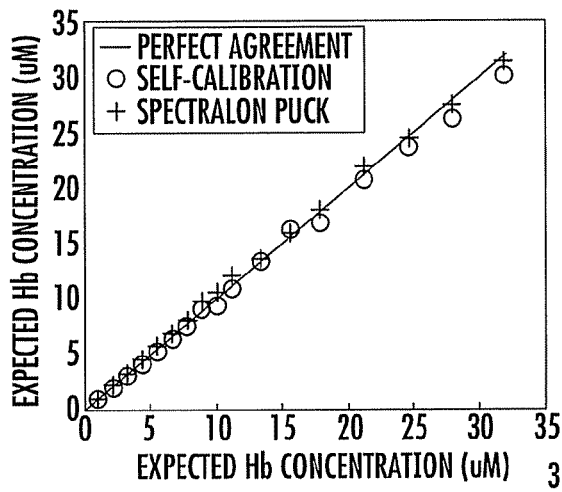
FIGS. 7A to 7B illustrate graphical data associated with optical spectroscopy sensors, systems and methods disclosed herein.
Figure 7B:
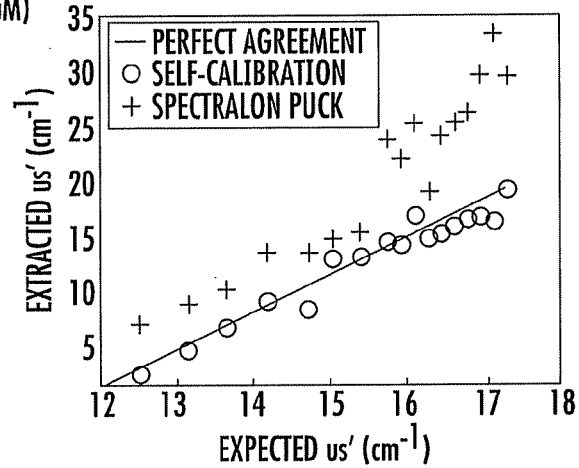

A non-transitory computer readable medium comprising computer executable instructions, that when executed by a processor of a computer 318, can perform steps comprising collecting spectra from the specimen, calculating and displaying probe pressure for the operator to manually adjust it, adjusting integration time, as necessary, calibrating the sample spectrum, perform spectral analysis, and display the extracted specimen optical properties and physiological parameters. In one aspect, data can be automatically stored if and only if pressure is within an optimal range and upon successful calibration. An optimal range can comprise a minimal optimal range wherein spectral data will be minimally affected by the contact pressure. It is anticipated that an optimal range will comprise 0 to 20 or 0 to 30 psi. The optimal range can comprise a preset value for a processing unit to base decisions off of. For example a processing unit can automatically analyze and save specimen spectral data if contact pressure is within the Minimal optimal range. The minimal optimal range will likely be dependent on the type of tissue analyzed (e.g., cervical, oral) and the underlying tissue compositions. Computer executable instructions can control the smart fiber optic system, load reference phantom and default parameters (such as integration time and desired pressure range), collect spectra from specimen and pressure sensor, calculate and display the probe pressure for the operator to manually adjust it, adjust integration time, calibrate the sample spectrum, perform spectral analysis, and display the extracted tissue optical properties and physiological parameters. It is expected that the time required to measure and analyze the spectra from a specimen be less than 2 seconds FIGS. 7A and 7B illustrate extracted vs. expected Hb concentrations and wavelength-averaged $\mu_s'$ obtained using different calibration techniques (conventional calibration is illustrated by the "+" puck and self-calibration is illustrated by the "o"). For example, homogeneous phantoms were evaluated and contained variable concentrations of hemoglobin (Hb), for example H0267 available from Sigma Co., as the absorber and 1-μm polystyrene spheres, for example, spheres available from Polysciences, Inc., as the scatterer. The $\mu_a$ was determined from a spectrophotometer measurement of a diluted Hb stock solution and the $\mu_s'$ was calculated using Mie Theory [13] for known size, density and refractive index of the scatterers. Two sets of phantoms with identical $\mu_s'$ were obtained through 17 successive titrations of the Hb from 1.01 to 31.87 μM in Day 1 and 0.91 to 29.71 μM in Day 2. Although the number of scatterers was fixed, the wavelength-averaged $\mu_s'$ over 450-600 nm decreased from 17.33-12.52 cm$^{-1}$ with successive dilution. A diffuse reflectance spectrum can be measured with a calibration spectrum concurrently from each phantom using the SC probe. Measurements taken after and during the lamp warm-up on Day 1 and 2, respectively and a spectrum was also measured from a 99% reflecting Spectralon puck immediately after the measurements of all 17 phantoms using identical integration time as for the phantom measurements. Approximately 45-60 minutes elapsed between the first phantom and the puck measurement. The phantom spectra were calibrated by dividing the tissue spectrum by the calibration spectra obtained with both the puck and the SC measurement for comparison. A phantom with mid-level $\mu_a$ and $\mu_s'$ was selected as the reference. The calibrated tissue spectrum was further normalized to the similarly calibrated reference phantom spectrum prior to analysis by a fast, scalable inverse Monte Carlo (MC) model to extract the tissue optical properties [9]. The calibration of the tissue spectrum against a reference phantom is needed to put the experimental and MC modeled data on the same scale, while the calibration of the tissue and reference phantom spectra to the puck or calibration spectrum is carried out to account for day to day variations in system throughput.

Inversions were performed in the wavelengths range of 450-600 nm using across-days data analysis, in which the target and reference phantoms were from the different days (representative of what would happen in an actual clinical setting).

TABLE 1

| Target/Reference | Spectralon Puck | | Self-Calibration | |
|---|---|---|---|---|
| | Day 1/2 | Day 2/1 | Day 1/2 | Day 2/1 |
| Error in [Hb] | 8.4 +/− 4.9% | 4.5 +/− 1.5% | 7.0 +/− 4.4% | 8.6 +/− 3.9% |
| Error in μs' | 9.0 +/− 3.2% | 12.5 +/− 6.1% | 3.8 +/− 3.4% | 2.1 +/− 1.1% |

Table 1 summarizes the errors in extraction of phantom Hb concentrations and $\mu_s'$ using different calibration techniques (puck vs. self-calibration). FIGS. 7A and 7B show the extracted vs. expected Hb concentrations and wavelength-averaged $\mu_s'$ obtained using Day 2 as the targets (corresponding to the second column under each calibration in Table 1). With both calibration techniques, the Hb concentrations can be extracted with reasonable accuracy. However, the errors for scattering are significantly reduced (2.3-6) times with the self-calibration, compared to the conventional (puck) calibration. Overall lamp intensity can vary over 25% in the first 30 minutes from lamp on, but the shape of the lamp spectrum had changed only slightly. The measurement of scattering is more sensitive to overall intensity while the measurement of absorption is more sensitive to the spectral shape. This data demonstrated the ability of the self-calibration using calibration channel 120 to correct for short- and long-term instrument fluctuations.

Figure 8:
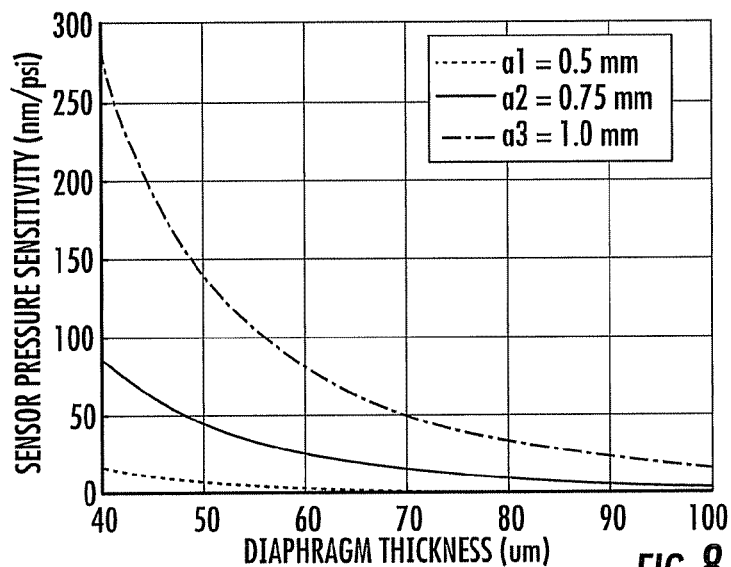
FIG. 8 illustrates graphical data associated with optical spectroscopy sensors, systems and methods disclosed herein.

As alluded to earlier, FIG. 8 illustrates sensor pressure sensitivity as a function of the diaphragm thickness at three diaphragm diameters, D=1.0 (a=0.5), 1.5 (a=0.75), and 2.0 mm (a=1.0). In general, it can be noted that sensitivity decreases with increasing diaphragm thickness, but the effect becomes less apparent at smaller diameters.

Figure 9:
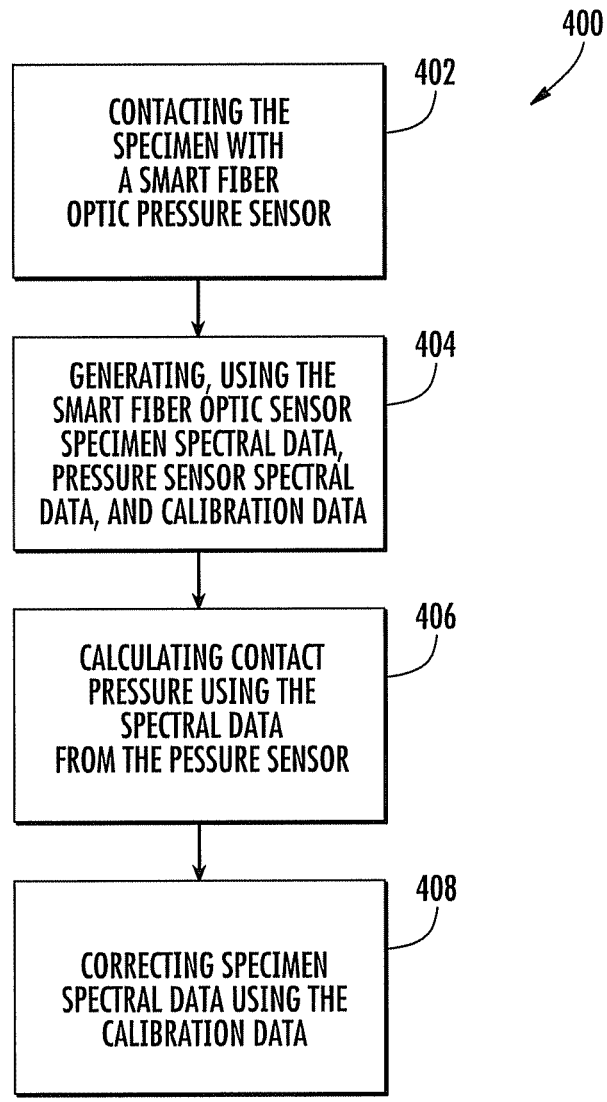
FIG. 9 illustrates flow chart illustrating an exemplary process for optical spectroscopy using smart fiber optic sensors and system disclosed herein.

FIG. 9 illustrates a flow chart for an exemplary process generally designated 400 for using smart fiber optic pressure sensors and system as described herein. Step 402 includes contacting the specimen with the smart fiber optic sensor. The pressure at which smart fiber optic sensor contacts the specimen, that is, contact pressure at a probe-specimen interface can be controlled using the smart fiber optic sensors and methods described herein, by calculating contract pressure from spectral data collected from a pressure sensor. Step 404 includes generating, using the smart fiber optic sensor, specimen spectral data, pressure sensor spectral data, and calibration data. Generating specimen spectral data can comprise transmitting a illumination light via at least one illumination fiber within the sensing channel from a first light source to the specimen and collecting the specimen spectral data using at least one detection fiber in the sensing channel, wherein the specimen spectral data can comprises the illumination light from the first light source diffusely reflected from the specimen at one or more wavelengths.

Step 406 includes calculating contact pressure using the spectral data from the pressure sensor. The pressure sensor can comprise a DFPI and pressure sensor spectral data can comprise reflectance data reflected along a cavity length of the DFPI. The pressure sensor can be disposed in a probe tip of the smart fiber optic sensor. Calculating pressure can comprise transmitting a low-coherence illumination light using a fiber optic fiber to a DFPI pressure sensor and collecting spectral data reflected by the pressure sensor via the same fiber optic fiber. As illustrated in FIG. 6, low-coherence light can propagate through the coupler to reach a lead in/out fiber. The output light from the DFPI can propagates through the coupler and a signal (from R1 and R2, FIG. 5) can be detected by the spectrometer that would be an interferogram from which the cavity length can be calculated using an algorithm. Cavity length can range from a few to several hundred micrometers. An external pressure (e.g., contact pressure with a specimen) can contact an outer surface of the diaphragm and bend the diaphragm toward the fiber and thus change the length of the air cavity. The applied pressure, or force, can therefore, be calculated by measuring the change of the cavity length from atmospheric pressure. A determination can be made regarding whether to analyze and save the spectral data from the sensing and calibration channels based on the pressure data. If pressure is not from a minimal preset range, the contact pressure may be too great thereby affecting specimen spectral data, thus, resulting in error and potentially inaccurate specimen data. Contact pressure at the probe/specimen interface can be adjusted and/or controlled such that the measured pressure stays within a specified, preset pressure range. In one aspect, the contact pressure can be controlled by an operator or technician based on real time pressure readings. As noted earlier, the first light source shared by sensing and calibration channels comprises a first emission spectra and the second light source utilized by the pressure sensing channel comprises a second emission spectra, and the first and second emission spectra do not overlap.

Step 408 includes correcting specimen spectral data using the calibration data. Correcting specimen spectral data can comprise transmitting calibration light via at least one calibration source fiber disposed in calibration channel, wherein the calibration light and the illumination light of the sensing channel can be generated simultaneously from the shared, first light source. Correcting specimen spectral data can further comprise collecting correcting spectral data associated with the calibration light via at least one calibration return fiber of the calibration channel contemporaneously with the collection of the spectral data of the specimen. The specimen spectral data received from the sensing channel can be corrected using the calibration spectral data received from the calibration channel.

Optional steps include analyzing and storing the specimen spectral data. Analyzing and storing the collected spectral data can comprise analyzing the calibrated spectral data to extract the specimen optical and physiological properties using, for example, an inverse MC model for reflectance. In one aspect, the data can be automatically analyzed and stored using a determination based upon the pressure data. If the pressure data is within a specified, preset range, then the specimen spectral data and calibration data can be automatically analyzed and/or stored.

In sum, it is describable to utilize a USB powered smart sensor system for performing in vivo quantitative DRS of soft tissues in wavelength range from 420-720 nm. The applications related to cancer screening in a global population can be greatly improved by the methods and systems disclosed herein. The smart sensor technology disclosed herein can incorporate innovations to several component areas. For example, white LEDs, miniature spectrometers, and a smart fiber-optic sensor can reduce the complexity, size, and cost of conventional optical spectroscopy systems. The systems and methods disclosed herein also minimize the amount of technical skill required to perform optical spectroscopy for early cancer detection applications. The compact integration of a tissue sensing portion, a pressure sensor, and a calibration portion into a single fiber-optic probe enables significant improvement in accuracy and robustness for extraction of tissue optical properties. By limiting or controlling the probe pressure and performing real-time calibration both systematic and random errors in reflectance measurements can be reduced. Further, the sensitivity and specificity for early cancer diagnosis can be improved.

Although the smart sensor discussed herein can be useful for screening and diagnostics for cancers such as oral and cervical cancers, it is not limited thereto. The systems and methods disclosed can be translated to other organ sites, such as the skin, bladder, etc. and can also be used for non-cancer applications such as monitoring vital signs during major surgeries in an intra-operative setting. The systems and methods disclosed herein can be used for any optical spectroscopy application known now or in the future.

The disclosure of each of the following references is hereby incorporated herein by reference in its entirety.

REFERENCES

[1] Schwarz, R. A., W. Gao, D. Daye, M. D. Williams, R. Richards-Kortum, and A. M. Gillenwater, *Autofluorescence and diffuse reflectance spectroscopy of oral epithelial tissue using a depth-sensitive fiber-optic probe*. Appl Opt, 2008. 47(6): p. 825-34.

[2] Wang, A., V. Nammalavar, and R. Drezek, *Targeting spectral signatures of progressively dysplastic stratified epithelia using angularly variable fiber geometry in reflectance Monte Carlo simulations*. J Biomed Opt, 2007. 12(4): p. 044012.

[3] Liu, Q. and N. Ramanujam, *Sequential estimation of optical properties of a two-layered epithelial tissue model from depth-resolved ultraviolet-visible diffuse reflectance spectra*. Appl Opt, 2006. 45(19): p. 4776-90.

[4] Utzinger, U. and R. R. Richards-Kortum, *Fiber optic probes for biomedical optical spectroscopy*. J Biomed Opt, 2003. 8(1): p. 121-47.

[5] Reif, R., M. S. Amorosino, K. W. Calabro, 0. A'Amar, S. K. Singh, and I. J. Bigio, *Analysis of changes in reflectance measurements on biological tissues subjected to different probe pressures*. J Biomed Opt, 2008. 13(1): p. 010502.

[6] Ti, Y. and W. C. Lin, *Effects of probe contact pressure on in vivo optical spectroscopy*. Opt Express, 2008. 16(6): p. 4250-62.

[7] Nichols, M. G., E. L. Hull, and T. H. Foster, *Design and testing of a white-light, steady-state diffuse reflectance spectrometer for determination of optical properties of highly scattering systems*. Appl Opt, 1997. 36(1): p. 93-104.

[8] Marin, N. M., N. MacKinnon, C. MacAulay, S. K. Chang, E. N. Atkinson, D. Cox, D. Serachitopol, B. Pikkula, M. Follen, and R. Richards-Kortum, *Calibration standards for multicenter clinical trials of fluorescence spectroscopy for in vivo diagnosis*. J Biomed Opt, 2006. 11(1): p. 014010.

[9] Palmer, G. M. and N. Ramanujam, *Monte Carlo-based inverse model for calculating tissue optical properties. Part I: Theory and validation on synthetic phantoms*. Appl Opt, 2006. 45(5): p. 1062-71.

[10] Yu, B., D. W. Kim, J. Deng, H. Xiao, and A. Wang, *Fiber Fabry-Perot sensors for detection of partial discharges in power transformers*. Appl Opt, 2003. 42(16): p. 3241-50.

[11] Yu, B., A. Wang, G. Pickrell, and J. Xu, *Tunable-optical-filter-based white-light interferometry for sensing*. Opt Lett, 2005. 30(12): p. 1452-4.

[12] Xu, J., G. R. Pickrell, B. Yu, M. Han, Y. Zhu, X. Wang, K. L. Cooper, and A. Wang. *Epoxy-free high temperature fiber optic pressure sensors for gas turbine engine applications in Sensors for Harsh Environments.* 2004: Proc. of SPIE. Vol. 5590.

[13] Prahl, S., *Mie scattering program.* 2005, Oregon Medical Laser Center, available at http://omlc.ogi.edu/software/mie/index.html.

What is claimed is:

1. A smart fiber optic sensor comprising:
a sensing channel for illuminating a specimen and for collecting spectral reflections from the specimen from which specimen spectral data can be determined;
a pressure sensing channel for collecting pressure sensor spectral reflections from which a contact pressure can be determined;
a calibration channel for obtaining calibration spectral reflections usable for correcting the specimen spectral data; and
a first light source for transmitting light having a first emission spectra to the sensing channel and calibration channel and a second light source for transmitting light having a second emission spectra to the pressure sensing channel, wherein the first and second emission spectra are non-overlapping.

2. The sensor according to claim 1, wherein the pressure sensing channel comprises a fiber optic pressure sensor.

3. The sensor according to claim 2, wherein the fiber optic pressure sensor comprises a diaphragm-based Fabry-Perot interferometric (DFPI) pressure sensor.

4. The sensor according to claim 3, further comprising a processing unit for calculating the contact pressure based on the cavity length of the DFPI from the pressure sensor spectral reflections.

5. The sensor according to claim 4, wherein the processing unit determines whether to save the specimen spectral reflections based on the contact pressure.

6. The sensor according to claim 1, wherein the sensing channel comprises at least one illumination fiber for transmitting light from the first light source to the specimen for generating the specimen spectral reflections.

7. The sensor according to claim 6, wherein the sensing channel comprises at least one detection fiber for detecting light diffusely reflected from the specimen at one or more wavelengths and communicating the diffusely reflected light from the specimen.

8. The sensor according to claim 6, wherein the calibration channel comprises:
a reflector;
at least one calibration source fiber for communicating calibration light from the first light source to the reflector;
at least one calibration return fiber for communicating the calibration spectral reflections from the reflector; and
a spectrometer for receiving the calibration spectral reflections and for generating calibration spectral data, wherein the calibration light and the first illumination light are generated simultaneously from the first light source.

9. The sensor according to claim 8, wherein the spectrometer generates the calibration spectral data based on the calibration light contemporaneously with the collection of spectral reflections from the specimen.

10. A smart fiber optic sensor system comprising:
a smart fiber optic sensor comprising:
a sensing channel for illuminating a specimen and for collecting spectral reflections from the specimen from which specimen spectral data can be determined;
a pressure sensing channel for collecting pressure sensor spectral reflections from which a contact pressure can be determined; and
a calibration channel for obtaining calibration spectral reflections usable for correcting the specimen spectral data, wherein the calibration channel comprises:
a reflector;
at least one calibration source fiber for communicating calibration light from the first light source to the reflector;
at least one calibration return fiber for communicating the calibration spectral reflections from the reflector; and
a spectrometer for receiving the calibration spectral reflections and for generating calibration spectral data, wherein the calibration light and the first illumination light are generated simultaneously from the first light source; and
a processing unit, coupled to the each of the sensing channel, the pressure sensing channel, and the calibration channel, the processing unit being adapted to receive and correct the specimen spectral data and to calculate a contact pressure at a sensor/specimen interface.

11. The sensor system according to claim 10, wherein the contact pressure at the sensor/specimen interface is calculated real time.

12. The sensor system according to claim 11, wherein the processing unit calculates and displays the contact pressure real-time by determining a cavity length of the DFPI using the spectral reflections obtained by the pressure sensing channel.

13. The sensor system according to claim 12, wherein the spectrometer generates calibration spectral data based on the calibration spectral reflections contemporaneously with the detection of spectral reflections from the specimen.

14. The sensor system according to claim 10, wherein the pressure sensing channel comprises a diaphragm-based Fabry-Perot interferometric (DFPI) pressure sensor.

15. The sensor according to claim 10, wherein the sensing channel further comprises at least one illumination fiber for transmitting light from a first light source to the specimen used for generating the specimen spectral data, at least one detection fiber for communicating light diffusely reflected from the specimen at one or more wavelengths, and a spectrometer for receiving the light diffusely reflected from the specimen and generating the specimen spectral data.

16. The sensor according to claim 10, wherein the spectrometer generates the calibration spectral data associated with the calibration light contemporaneously with the collection of the spectral reflections from the specimen.

17. The sensor system according to claim 16, wherein the processing unit analyzes the calibrated specimen spectral data and stores the calibrated specimen spectral data if the contact pressure is within a predetermined range.

18. A method for utilizing a smart fiber optic sensor for measuring a specimen, the method comprising:
contacting the specimen with the smart fiber optic sensor;
generating, using the smart fiber optic sensor, specimen spectral data, pressure sensor spectral data, and calibration spectral data, wherein generating the specimen spectral data comprises:

transmitting a first illumination light via at least one illumination fiber from a first light source to the specimen;

collecting spectral reflections at a spectrometer using at least one detection fiber, the specimen spectral reflections comprising the first illumination light diffusely reflected from the specimen at one or more wavelengths; and generating, using the spectrometer, the specimen spectral data based on the reflections; and wherein generating the calibration spectral data comprises:

transmitting calibration light to a reflector via at least one calibration source fiber, wherein the calibration light and the first illumination light are generated simultaneously from the first light source;

collecting calibration spectral reflections at the spectrometer using at least one calibration return fiber; and generating, using the spectrometer, the calibration spectral data from the calibration reflections;

calculating a contact pressure at an interface of the smart fiber optic sensor and the specimen using the pressure sensor spectral data; and correcting specimen spectral data using the calibration spectral data.

19. The method according to claim 18, further comprising analyzing and storing the specimen spectral data.

20. The method according to claim 19, wherein analyzing and storing the collected spectral data comprises analyzing the corrected specimen spectral data to extract optical and physiological properties from the specimen using an inverse Monte Carlo model for reflectance.

21. The method according to claim 18, wherein generating the pressure sensor spectral data comprises:

transmitting a second illumination light using at least one optical fiber to a diaphragm-based Fabry-Perot interferometric (DFPI) pressure sensor; and collecting pressure sensor spectral reflections reflected by the pressure sensor at the spectrometer via the same optical fiber; and generating, using the spectrometer, the pressure sensor spectral data based on the pressure sensor spectral reflections.

22. The method according to 21, wherein calculating the contact pressure comprises:

determining the cavity length of the DFPI using the pressure sensor spectral data;

calculating a contact pressure of the DFPI/specimen interface using the cavity length of the DFPI.

23. The method according to claim 18, further comprising determining whether to analyze and save the specimen spectral data based on the calculated contact pressure.

24. The method according to claim 18, further comprising adjusting a pressure at which the smart fiber optic sensor contacts the specimen such that the contact pressure stays within an optimal preset pressure range.

25. The method according to claim 18, wherein emission spectra respectively used to determine the specimen spectral data and the contact pressure are non-overlapping.

* * * * *